US012801776B1

(12) United States Patent
Wang et al.

(10) Patent No.: US 12,801,776 B1
(45) Date of Patent: Nov. 17, 2026

(54) SYSTEMS AND METHODS FOR PROVIDING SECURE MULTI-TIERED ACCESS TO UNMASKED DATA

(71) Applicant: Veeva Systems Inc., Pleasanton, CA (US)

(72) Inventors: Ying Zhuo Wang, Toronto (CA); Marius K. Mortensen, Burlington (CA); Zhen Tan, North York (CA); Bradley Arnold, Lakewood, CO (US); Petra Schmitz, Mississauga (CA)

(73) Assignee: Veeva Systems Inc., Pleasanton, CA (US)

( * ) Notice: Subject to any disclaimer, the term of this patent is extended or adjusted under 35 U.S.C. 154(b) by 20 days.

(21) Appl. No.: 18/742,007

(22) Filed: Jun. 13, 2024

(51) Int. Cl.
*G06F 21/62* (2013.01)
*G16H 50/70* (2018.01)

(52) U.S. Cl.
CPC ......... *G06F 21/6245* (2013.01); *G16H 50/70* (2018.01)

(58) Field of Classification Search
CPC ............................ G06F 21/6245; G16H 50/70
See application file for complete search history.

(56) References Cited

U.S. PATENT DOCUMENTS 5,197,005 A 3/1993 Shwartz et al.
10,803,201 B1 * 10/2020 Nicholls ............. G06F 21/6227
2003/0233250 A1 12/2003 Joffe et al.
2004/0243545 A1 12/2004 Boone et al.
2006/0129427 A1 6/2006 Wennberg
2008/0147554 A1 6/2008 Stevens et al.
2010/0083358 A1 * 4/2010 Govindarajan ......... H04L 63/08 726/6
2010/0179831 A1 * 7/2010 Brown .................... G16Z 99/00 713/170
2011/0015942 A1 1/2011 Oakley et al.
2011/0184250 A1 7/2011 Schmidt et al.
2012/0209624 A1 * 8/2012 Maitland ................ G16H 10/60 705/3
2013/0054264 A1 2/2013 Baronov et al.
2014/0074510 A1 3/2014 McClung et al.
2014/0095469 A1 4/2014 Chen et al.
2014/0114952 A1 4/2014 Robinson et al.
2014/0164439 A1 * 6/2014 Gale ..................... G06F 16/242 707/803
2014/0236628 A1 * 8/2014 Friese .................... G16H 30/20 705/3
2014/0257047 A1 9/2014 Sillay et al.
2015/0317435 A1 11/2015 Klocek et al.
(Continued)

*Primary Examiner* — Mohamed A. Wasel

(57) ABSTRACT

A method for generating a case dataset includes receiving a source file including medical product data and determining case data including the medical product data based on the source file. The method includes generating the case dataset including the case data. The method further includes generating a copy of the medical product data and modifying the copy of the medical product data to generate unblinded medical product data. The method further includes adding the unblinded medical product data to the case data of the case dataset. The method further includes storing the case dataset in the first repository and outputting the case dataset including a portion of the case data. The portion of the case data includes the blinded medical product data and does not include the unblinded medical product data.

18 Claims, 9 Drawing Sheets

(56) References Cited

U.S. PATENT DOCUMENTS

| | | | | |
|---|---|---|---|---|
| 2016/0085914 | A1 | 3/2016 | Douglass et al. | |
| 2016/0125000 | A1 | 5/2016 | Meacham et al. | |
| 2016/0147945 | A1* | 5/2016 | MacCarthy | H04W 12/02 705/51 |
| 2017/0039280 | A1 | 2/2017 | Kapse | |
| 2017/0208041 | A1* | 7/2017 | Kho | G16H 10/60 |
| 2019/0034590 | A1 | 1/2019 | Oren et al. | |
| 2020/0350068 | A1* | 11/2020 | Helmer | G16H 40/67 |
| 2021/0240694 | A1 | 8/2021 | Mortensen et al. | |
| 2025/0252162 | A1* | 8/2025 | Abburi | G06F 21/604 |

* cited by examiner

400

SYSTEMS AND METHODS FOR PROVIDING SECURE MULTI-TIERED ACCESS TO UNMASKED DATA

TECHNICAL FIELD

The present disclosure relates to systems and methods for providing secure multi-tiered access to unmasked data.

BACKGROUND

Researchers, scientists, industry players, academics, government regulators, and other stakeholders are increasingly in need of efficient and simple ways to unmask masked data and provide secure access to the unmasked data.

SUMMARY

One embodiment relates to a method for generating a case dataset in a case dataset intake and management system. The case intake and management system includes a provider computing system. The provider computing system includes a first repository for storing case datasets. The method includes receiving a source file including medical product data and determining case data including the medical product data based on the source file. The method includes generating the case dataset including the case data. The method further includes generating a copy of the medical product data and modifying the copy of the medical product data to generate unblinded medical product data. The method further includes adding the unblinded medical product data to the case data of the case dataset. The method further includes storing the case dataset in the first repository and outputting the case dataset including a portion of the case data. The portion of the case data includes the blinded medical product data and does not include the unblinded medical product data.

Another embodiment relates to a method for generating a case dataset in a case dataset intake and management system. The case intake and management system includes a provider computing system. The provider computing system includes a first repository for storing case datasets. The method includes receiving a source file including blinded medical product data and determining case data including the blinded medical product data based on the source file. The method includes generating the case dataset including the case data. The method further includes generating a copy of the blinded medical product data and modifying the copy of the medical product data to generate unblinded medical product data. The method further includes adding the unblinded medical product data to the case data of the case dataset. The method further includes storing the case dataset in the first repository and outputting the case dataset including a portion of the case data. The portion of the case data includes the blinded medical product data and the unblinded medical product data.

This summary is illustrative only and is not intended to be in any way limiting. Other aspects, inventive features, and advantages of the devices or processes described herein will become apparent in the detailed description set forth herein, taken in conjunction with the accompanying figures, wherein like reference numerals refer to like elements.

DETAILED DESCRIPTION

Figure 1:
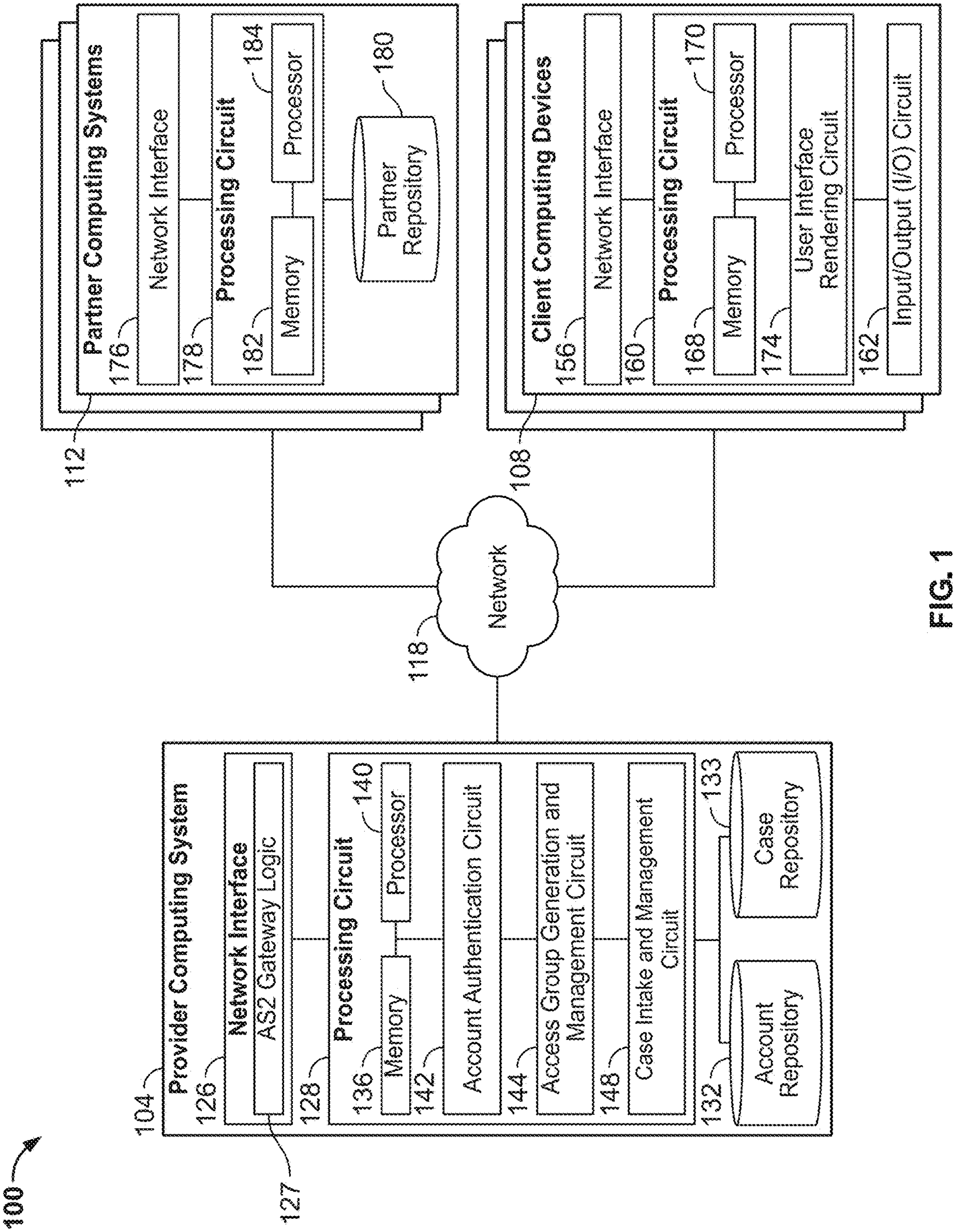
FIG. 1 may be a component diagram of a case dataset intake and management system, according to an example embodiment.

Referring generally to the figures, systems and methods for providing secure multi-tiered access to unmasked or unblinded data are disclosed. The systems and method described herein provide for improved data security by providing isolation between the unblinded/unmasked medical product data and the blinded/masked medical product data. For instance, because the systems and methods generate a copy of the blinded medical product data and then unblind the copy of the blinded medical product data, the present system and methods create two, isolated, sets of medical product data: one masked and one unmasked, which provides for an improvement to data security. For instance, by isolating masked data, the present systems and methods limit the amount of sensitive data an attacker can access if they breach a system's defenses. Even if they gain access to the masked data, it's useless without the key to unmask it. This compartmentalization minimizes potential data theft. Likewise, by controlling access to unmasked data through the case access groups, the present systems provide for stricter privilege levels. Only authorized or privileged users with a legitimate need would have access to the unmasking process. This reduces the risk of accidental exposure or unauthorized access. Furthermore, because the present systems and methods maintain data integrity by keeping a copy of the blinded or masked medical product data and the unblinded or unmasked medical product data, specific user's (e.g., those who do not have unmasked data privileges) can leverage masked data sets, reducing the need for the use and disclosure of sensitive data. This minimizes security risks during the case dataset generation and intake process.

Additionally, by generating a copy of the blinded medical product data and then unblinding the copy of the blinded medical product data, the present systems and methods keep a store of the blinded medical product data and the unblinded medical product data, and thereby provide for improved data integrity. For instance, by isolating blinded medical product data from unblinded medical product data, the present systems and methods create separation between the masked data and the original unmasked data. This separation minimizes the chance of accidentally modifying or corrupting the sensitive data during processing or storage. Likewise, because the masked medical product data is stored independently of the unmasked medical product data, the present systems and methods track and monitor changes to the masked medical product data more easily, thereby identifying any unauthorized access or manipulation attempts and making it easier to maintain an audit trail for data integrity purposes.

Likewise, the systems and methods described herein provide for enhanced security of case datasets by providing for multi-tiered and dynamic access to case datasets via case access groups, thereby helping and improving the pharmacovigilance industry by more accurately and securely providing for the intake and reporting of case datasets to health authorities. For example, by assigning one or more users and one or more case datasets to a specific case access group, the present systems and methods provide for multi-tiered access to case datasets that are within the user's case access group and prevent access to case datasets that are outside of the user's case access group. In comparison, typical case intake systems may not distinguish between users when providing access to groups, thereby allowing users to access a variety of case datasets for which they may not be authorized to view and/or edit. In comparison, the present systems and methods may assign one or more specific user's and/or roles (e.g., job titles) in specific regions (e.g., US, China, Asia, Europe) to case access groups and then assign case datasets which are relevant and for which the users are authorized to access to the case access groups. Then, in response to the authenticating the user (e.g., via a username and password), the present systems and methods may provide the relevant case datasets to the user. By doing so, the present systems and methods prevent unauthorized access to case datasets and provide for a more dynamic and secure system in which the admin(s) can set the specific permission (and case datasets) each user has access to, which results in less cases being stolen, ending up in the wrong hands, or being handled by the wrong user(s), thereby improving case security.

As used herein, the term "event," "medical event," or "adverse event" can include any untoward medical occurrence which happens to either a patient or a subject in a clinical investigation or during regular use of a medical product that has been given to that person. For example, the "event," "medical event," or "adverse event" may encompass any signs which are unfavorable and unexpected for the patient or subject, including any abnormal laboratory findings such as a high blood pressure, a rapid heart rate, etc. The "event," "medical event," or "adverse event" could be symptoms, or a disease temporally associated with the use of a medical product and does not have to have been previously associated with that product. The term "event," "medical event," or "adverse event" can further encompass adverse reactions and serious adverse events such as death, life-threatening adverse experiences, inpatient hospitalization, congenital birth defects, disabilities, etc. Further, each "event," "medical event," or "adverse event" may be defined by the Medical Dictionary for Regulatory Activities (MedDRA) (or other medical code dictionaries) and associated with a specific MedDRA code. Moreover, "event information" "medical event information" "adverse event information" "event data" "medical event data" or "adverse event data" can include information associated with the event such as the date of onset of the event, the date of cessation of the event, the type of event, the dictionary (i.e., digital dictionary, medical dictionary, digital medical dictionary, etc.) or medical term (e.g., MedDRA term), the dictionary or medical code (e.g., MedDRA code), event comments, the outcome of the event, the location of the event (e.g., country where the event occurred), the event duration, patient data for a patient who endured or to which the event occurred, medical products that the patient consumed and/or dosages for the consumed medical products, the event rank, event contacts, the event type, and any associated event documents.

Likewise, as used herein, the "blinded medical product data" or "masked medical product data" may include a placeholder, token, or other value in place of the actual medical product name or substance (e.g., "xxx" in place of "Drug X," a token or hash (e.g., 12345) in place of "Drug X," "Blinded" in place of "Drug X," etc.), as well as the medical product identifier (e.g., National Drug Code (NDC), dosages, form (e.g., capsule, intravenous, etc.), and other medical product data, to prevent the identification of the blinded medical product of the blinded medical product data.

As used herein, the term "case" or "case dataset" can include an Individual Case Safety Report (ICSR) as defined by the standard ISO/HL7 27953 of the International Standards Organization (ISO) as well as any past or future standards governing ICSRs of the ISO, the World Health Organization (WHO), the Food and Drug Administration (FDA), the European Medicines Agency (EMA), or other national health agencies governing ICSRs. Moreover, "case information" "case data" or "case dataset" can include information associated with or included in the case such as adverse event data, case contact data, case identifier (e.g., case worldwide ID (WWID), case number, etc.), case priority data, case seriousness data, case documents, medical product data, medical product registrations, patient data, and other data associated with a case as defined by the standard ISO/HL7 27953 as well as any past or future standards governing ICSRs of the ISO, the WHO, the FDA, the EMA, or other national health agencies governing ICSRs.

Referring now to FIG. 1, a system 100 for providing secure multi-tiered access to blinded medical product data is shown, according to an example embodiment. The system 100 includes a provider computing system 104, multiple client computing devices 108, and one or more partner computing systems 112 connected by a secure network (e.g., a network 118).

The network 118 communicably and operably couples the provider computing system 104, the client computing devices 108, and the partner computing systems 112 such that communicable and operable computing may be provided between the provider computing system 104, the client computing devices 108, and the partner computing systems 112 over the network 118. In various embodiments, the network 118 includes any combination of a local area network (LAN), an intranet, the Internet, or any other suitable communications network, directly or through another interface.

The provider computing system 104 may be operated and managed by a provider (e.g., a software as a service (SaaS) provider, a cloud services provider, a software provider, a service provider, etc.) and may include a computer system (e.g., one or more servers (e.g., a cloud computing server) each with one or more processing circuits). In some embodiments, the provider computing system 104 may act as a host and provide an application (e.g., a web-based application, a mobile application, etc.) to the client computing device 108 over the network 118 in response to authenticating the respective computing device. For example, the provider computing system 104 may receive authentication data (e.g., a username and corresponding password, a limited-use key, a two-factor authentication code or key, etc.) from one of the client computing devices 108. The provider computing system 104 may then authenticate the client computing device 108 based on the authentication data and provide an application to the client computing device 108 over the network 118. In some examples, the provider computing system 104 may be a multi-tenant system where various elements of hardware and software may be shared by one or more customers. In a multi-tenant system, a user is typically associated with a particular customer. In one example, a user (e.g., of the client computing device 108) could be an employee of one of a number of (pharmaceutical) companies which are tenants, or customers, of the provider computing system 104.

In some embodiments, the provider computing system 104 may run on a cloud computing platform. Users can access content on the cloud independently by using a virtual machine image or purchasing access to a service maintained by a cloud repository provider.

In some embodiments, the provider computing system 104 may be provided as Software as a Service ("SaaS") to allow users to access the provider computing system 104 with a thin client.

As shown, the provider computing system 104 may include a network interface 126, a processing circuit 128, an account repository 132, and a case repository 134. In some embodiments, the provider computing system 104 includes a medical product repository (not shown). In some embodiments, the provider computing system 104 may include an input/output circuit (e.g., similar to (e.g., the same as) an input/output circuit 162 as will described further herein).

The network interface 126 is structured to establish connections with the client computing devices 108 and/or the partner computing systems 112 by way of the network 118. The network interface 126 includes program logic (e.g., AS2 Gateway Logic 127) and/or hardware-based components that connect the provider computing system 104 to the network 118. For example, the network interface 126 may include any combination of a wireless network transceiver (e.g., a cellular modem, a broadband modem, a Bluetooth transceiver, a Wi-Fi transceiver, a Li-Fi transceiver, etc.) and/or a wired network transceiver (e.g., an Ethernet transceiver). In some embodiments, the network interface 126 includes the hardware and machine-readable media structured to support communication over multiple channels of data communication (e.g., wireless, Bluetooth, near-field communication (NFC). In some embodiments, the network interface 126 includes cryptography logic and capabilities to establish a secure communications session.

The AS2 gateway logic 127 includes programmable instructions that facilitate communication (transmission and receipt) using the Applicability Statement 2 (AS2) communication protocol (as specified in Request for Comment (RFC) 4130) over the network 118 via the network interface circuit 126. For example, using the AS2 gateway logic 127, the network interface 126 may transmit or receive files (e.g., the source file, a case, etc.) or other data to the partner computing systems 112 or the client computing devices 108 using the AS2 Gateway protocol. In other embodiments, the AS2 gateway logic 127 may transmit or receives files using the most updated Applicability Statement communication protocol (e.g., AS3, etc.).

The processing circuit 128, as shown, comprises a memory 136, a processor 140, an account authentication circuit 142, an access group generation and management circuit 144, and a case intake and management circuit 148. The memory 136 includes one or more memory devices (e.g., RAM, NVRAM, ROM, flash memory, hard disk storage, etc.) that store data and/or computer code for facilitating the various processes described herein. That is, in operation and use, the memory 136 stores at least portions of instructions and data for execution by the processor 140 to control the processing circuit 128. The memory 136 may be or include tangible, non-transient volatile memory and/or non-volatile memory. The processor 140 may be implemented as a general-purpose processor, an application specific integrated circuit (ASIC), one or more field programmable gate array (FPGAs), a digital signal processor (DSP), a group of processing components or other suitable electronic processing components.

As described herein, the account authentication circuit 142 (also referred to as account gateway circuit 142) is structured or configured to receive authentication data, authenticate the authentication data, and associate the client computing device 108 from which the authentication data was received with specific permissions. For instance, the account authentication circuit 142 may be configured or structured to receive authentication data (e.g., username and password, electronic address (e.g., IP address, FTP address, or other addresses from which the authentication data is received), limited-use key, etc.) from a client computing device 108 during a log-in process. The account authentication circuit 142 may then authenticate the authentication data by determining if the authentication data matches authentication data stored in the account repository 132. Then, in response to authenticating the client computing device 108, the account authentication circuit 142 may assign or associate specific permissions (e.g., a specific case access group, admin permissions, regular user permissions, etc.) to the client computing device 108 based on the received authentication data. For instance, the authentication data may indicate the client computing device 108 is associated with the user (John Smith) based on the authentication data received from the client computing device 108 (e.g., the username and password associated with John Smith). Accordingly, the account authentication circuit 142 may assign the client computing device 108 the permissions associated with the authentication data and John Smith. In another example, the authentication data may indicate the client computing device 108 is associated with administrator (admin) user (Jane Doe) based on the authentication data received from the client computing device 108 (e.g., the username and password associated with Jane Doe). The provider computing system 104 may then assign admin permissions to the client computing device 108 associated with Jane Doe, as will be described further herein.

In some embodiments, the account authentication circuit 142 may assign the permissions to the electronic address of the client computing device 108 for a specific period of time. In this regard, when a request is received from the electronic address, the provider computing system 104 may determine the client computing device 108 has the specific permissions based on electronic address. Then, when the specific period of time has passed, the client computing device 108 may again provide authentication data. In other embodiments, the account authentication circuit 142 may provide the authentication data to the access group management circuit 144 which may assign the permissions to the client computing device 108.

The access group generation and management circuit 144 is structured or configured to generate and manage case dataset access groups. For example, the access group generation and management circuit 144 may receive case dataset assignment data (e.g., all US cases, all marketed medical products, all medical products that are currently within a study, all cases that need to be reported to the FDA, etc.) and user assignment data (e.g., John Smith, Jacob Smith, Teresa Smith, etc.) from the client computing device 108. In response, the access group generation and management circuit 144 may generate an access group that includes each and store the access group within the account repository 132. Then, the provider computing system 104 may parse through each case dataset in the case repository 134 and assign one or more of the case datasets to the access group based on the case dataset assignment data. In some embodiments, the access group generation and management circuit 144 may further search the account repository 132 for each user of the user assignment data and assign each user to the access group.

As described herein, the case intake and management circuit 148 is structured or configured to receive, generate, store, and manage case datasets. For instance, the case intake and management circuit 144 may be configured or structured to receive or retrieve a source file including adverse event data associated with an adverse event from a trusted source (one of the client computing devices 108, a partner computing system (e.g., the FDA Gateway) (not shown), etc.). The case intake and management circuit 148 may then match the adverse event data with medical product data of a medical product repository (not shown), generate a case dataset including case data, and store the case dataset within the case repository 134. In one example, the case intake and management circuit 144 may be an instance of Vault Safety®.

In some embodiments, the adverse event data may include medical product data associated with the adverse event and a blind field indicating the medical product data is to be blinded. In response, the case intake and management circuit 148 may be configured or structured to receive medical product data and modify the medical product data to generate blinded medical product data (also referred to as masked or token medical product data). As described herein, the blinded medical product data may include a placeholder, token, or other value in place of the actual medical product name or substance (e.g., "xxx" in place of "Drug X," a token or hash (e.g., 12345) in place of "Drug X," "Blinded" in place of "Drug X," etc.), as well as the medical product identifier (e.g., National Drug Code (NDC), dosages, form (e.g., capsule, intravenous, etc.), and other medical product data, to prevent the identification of the blinded medical product. Then, in response to receiving a request to unblind or reveal the blinded medical product data, the case intake and management circuit 148 may generate a copy of the blinded medical product data and modify the copy of the blinded medical product data to generate unblinded medical product data. The unblinded medical product data may be the same as the medical product data and include the authentic or genuine medical product name (e.g., Drug X) or substance, medical product identifier (e.g., NDC 123), dosage (e.g., 500 Mg), form (e.g., capsule), and other medical product data.

In some embodiments, the provider computing system 104 may include a medical product repository (not shown) where medical product data is stored. In other embodiments, the medical product data may be stored in the case repository 133. Then, in response to receiving medical product data associated with a blinded medical product and/or blinded study, the provider computing system 104 may modify the medical product data to generate blinded medical product data by tokenizing or hashing the medical product data. For instance, the provider computing system 104 may generate a token associated with the unblinded medical product data. The token may be a random string of letters and numbers that has no inherent value on its own, which takes the place of the medical product data as blinded medical product data. Then, the original medical product data may be stored in the medical product data in association with the token, and the blinded medical product data (e.g., the token) may be stored in the case dataset. Accordingly, to generate the unblinded medical product data, the provider computing system 104 may retrieve the medical product data, associated with the blinded medical product data (e.g., the token), from the medical product repository (not shown).

In another example, to generate blinded medical product data by encrypting the medical product data, the provider computing system 104 may use an encryption function (e.g., a Symmetric Encryption Algorithm, an Asymmetric Encryption Algorithm, etc.) and a first key (e.g., a private key) to transform each piece of medical product data into blinded medical product data (e.g., a ciphertext). Then, to unblind the blinded medical product data, the provider computing system may use a second key (e.g., a public key) to unblind or decrypt the blinded medical product data and generate the unblinded medical product data.

In some embodiments, the case intake and management circuit 144 the received adverse event data may include blinded medical product data (as compared to unblinded or medical product data) and store the blinded medical product data therein (e.g., in the case repository 133, in a medical product repository (not shown), etc.). Then, in response to receiving a request to unblind or reveal the blinded medical product data, the case intake and management circuit 148 may generate a copy of the blinded medical product data and modify the copy of the blinded medical product data to generate unblinded medical product data. For instance, the case intake and management circuit 148 may generate and provide an unblinded data request to one of the partner computing systems 112. The request may include authentication data (e.g., a username, a passcode, a key, a case identifier, and/or the like). In response, the partner computing system 112 may provide the unblinded medical product data to the case intake and management circuit 148. In response, the case intake and management circuit 148 may replace the copy of the blinded medical product data with the unblinded medical product data. In some embodiments, the case intake and management circuit 148 may provide the request for the unblinded medical product data to the client computing device 108 from which the request to unblind or reveal the blinded medical product data was received. In response, the client computing device 108 may provide the unblinded medical product data to the case intake and management circuit 148. Then, the case intake and management circuit 148 may replace the copy of the blinded medical product data with the unblinded medical product data.

Additionally, the case intake and management circuit 148 may be configured or structured to retrieve cases from the case repository, in response to receiving a request including case criteria (e.g., a medical product of the case, a date of the case, a state of the case (e.g., open, closed, submitted, pending review), a country in which the case took place, etc.) from one of the client computing devices 108. The request may include or identify a sender address (e.g., an IP address, an FTP address, an email address) and/or authorization data. In response, the case intake and management circuit 148 may determine the case access group associated with the client computing device 108 and select one or more case datasets from the case repository 134 based on the case criteria and the case access group. In some embodiments, the case intake and management circuit 148 may further modify the case dataset(s) based on the case access group. For instance, the case access group may indicate the user does not have access to personally identifying information (PII). Accordingly, the case intake and management circuit 148 may remove or mask any PII included in the case dataset(s) (e.g., patient name, patient date of birth, patient address, etc.).

The account repository 132 may be a repository (e.g., a database) that is structured or configured to receive, store, and manage accounts of users (e.g., of the client computing devices 112). In this regard, the account repository 132 may receive, store, and manage authentication data therein. For example, the account repository 132 may receive one or more new user accounts from one of the client computing device 112 including authorization data for each account (e.g., username, password, two-factor authorization contact addresses, etc.) and store the new user accounts therein. Then, in response to receiving a request for authentication data, the account repository 132 may output any matching authentication data. Accordingly, the account 132 can be structured according to various database types, such as, relational, hierarchical, network, flat, point-in time, and/or object relational. Further, the account repository 132 includes a plurality of nonvolatile/non-transitory storage media such as solid-state storage media, hard disk storage media, virtual storage media, cloud-based storage drives, storage servers, and/or the like.

In some embodiments, the account repository 132 may receive, store, and manage access groups and access group data (e.g., case dataset assignment data, user assignment data, etc.) therein. For instance, the access group generation and management circuit 144 may generate an access group including case dataset assignment data and one or more users and provide the access group to the account repository 132 for storage. The account repository 132 may store the access group with an association (e.g., a reference pointer or reference to) the one or more user(s) of the access group. For instance, the access group may include the users person 1, person 2, and person 3. Further, person 1 may be associated with or be assigned user account 1; person 2 may be associated with user account 2; and person 3 may be associated with user account 3. Accordingly, the access group may be associated with or include a reference pointer to account 1, account 2, and account 3, and vice versa. In other embodiments, the access group and the access group data may be stored and managed by an access group repository (not shown) that is separate from the account repository 132 (but may be structured the same).

Likewise, the case repository 134 may be repository (e.g., a database) that is structured or configured to receive, store, and manage case datasets and their respective data (e.g., case data, adverse event data, etc.). For example, the case repository 134 may receive case datasets and related case objects and store the case datasets therein. Then, in response to receiving a query or a request for one or more case datasets (e.g., a query for all cases that include a specific medical term and/or code) the case repository 134 may provide and/or return the case datasets stored therein that match the query or request. For example, the case repository 134 may receive a query from the case intake and management circuit 148 for all cases that include a specific criteria (e.g., a specific medical (MedDRA) code). In response, the case repository 134 may determine each case dataset that includes the specific medical code stored therein and return each case dataset. In some embodiments, the case dataset may include or identify the access group(s) to which the case dataset is assigned (e.g., based on the case dataset assignment data). Therefore, in another example, the case repository 134 may receive a query from the case intake and management circuit 148 for all cases that include a specific criteria (e.g., a specific medical product) and are assigned to a specific access group. In response, the case repository 134 may determine each case dataset that includes or is associated with the specific medical product and the specific access group therein and return each case dataset. Further, the case repository 134 can be structured according to various database types, such as, relational, hierarchical, network, flat, point-in time, and/or object relational. In some embodiments, the case repository 134 includes a plurality of nonvolatile/non-transitory storage media such as solid-state storage media, hard disk storage media, virtual storage media, cloud-based storage drives, storage servers, and/or the like. In some embodiments, the provider computing system 104 may include a separate case repository 134 for each customer or sponsor, thereby keeping the case datasets of each customer separate.

Still referring to FIG. 1, the client computing devices 108 can each be any type of computing device or computing system. For instance, each client computing device 108 can be one or more of a mobile phone, a tablet computer, a laptop computer, a smart watch, a server computer system, or any other internet-connected device. In operation, the client computing devices 108 may communicate and interface with the provider computing system 104 via the network 118 to provide authorization credentials and a request for case datasets including case criteria. In response, the provider computing system 104 may provide one or more case datasets to the respective client computing device 108. As shown, each client computing device 108 may include a network interface 156, a processing circuit 160, and the input/output (I/O) circuit 162.

As described herein, each client computing device 108 may be associated with a different user who may have a different role within a specific company (e.g., CEO, Chief Safety Officer (CSO), administrator, case processor (USA), case processor (EMA), medical reviewer, etc.). In this regard, each different user and associated client computing device 108 may be associated with a specific address (e.g., email address, IP address, etc.), a specific account, and a specific case access group. For example, the client computing device 108 associated with the CSO may be associated with the case access group (All Access) which has access to all case datasets; whereas the client computing device associated with a case processor (USA) may be associated with the case access group (Cases-USA) which has access to case datasets which originated (i.e., were first reported) in the USA or with a specific health agency (e.g., the FDA) and are to be submitted in the USA. In this regard, each client computing device 108 may have access to different case datasets (based on the case access group and the account of the user). For example, a first client computing device 108 may generate a request for case datasets with a first case criteria (e.g., a specific medical code) and receive a first set of case datasets. Then, a second client computing device 108 may generate a request for case datasets with a second case criteria that is the same as the first case criteria. The first client computing device 108 and the second client computing device 108 may be associated with different access groups. Accordingly, the second client computing device 108 may receive a second set of case datasets which is entirely different than the first set of case datasets.

The network interface 156 is structured to establish connections with the provider computing system 104 by way of the network 118. The network interface 156 includes program logic and/or hardware-based components that connect the client computing device 108 to the network 118. For example, the network interface 156 may include any combination of a wireless network transceiver (e.g., a cellular modem, a broadband modem, a Bluetooth transceiver, a Wi-Fi transceiver, a Li-Fi transceiver, etc.) and/or a wired network transceiver (e.g., an Ethernet transceiver). In some embodiments, the network interface 156 includes the hardware and machine-readable media structured to support communication over multiple channels of data communication (e.g., wireless, Bluetooth, near-field communication (NFC). In some embodiments, the network interface 156 includes cryptography logic and capabilities to establish a secure communications session.

The processing circuit 160, as shown, comprises a memory 168, a processor 170, and a user interface generation or rendering circuit 174. The memory 168 includes one or more memory devices (e.g., RAM, NVRAM, ROM, flash memory, hard disk storage, etc.) that store data and/or computer code for facilitating the various processes described herein. That is, in operation and use, the memory 168 stores at least portions of instructions and data for execution by the processor 170 to control the processing circuit 160. The memory 168 may be or include tangible, non-transient volatile memory and/or non-volatile memory. The processor 170 may be implemented as a general-purpose processor, an application specific integrated circuit (ASIC), one or more field programmable gate array (FPGAs), a digital signal processor (DSP), a group of processing components or other suitable electronic processing components.

The user interface rendering circuit 174 may be configured to receive a user interface (e.g., a web interface in an HTML file and related files, a downloaded graphical user interface, etc.) from the provider computing system 104 and render the user interface on the client computing device 108 via the I/O circuit 162. In this way, the provider computing system 104 may generate one or more user interfaces and provide the one or more user interfaces to the user interface generation circuit 174 to be rendered on the client computing device 108 (e.g., on a display of the I/O circuit 162 of the client computing device 108).

The I/O circuit 162 is structured to receive communications from and provide communications to the user of the client computing device 108 (e.g., the user). In this regard, the I/O circuit 162 is structured to exchange data with the processing circuit 160 to provide output to the user and to receive input from the user. As a result, the I/O circuit 162 may include a display that may be manipulated by the application. In some embodiments, the I/O circuit 162 may also include a keyboard, a mouse, a joystick, a touch screen, touch areas, soft keys, a microphone, a speaker, a vibration mechanism, a sensor, a RFID scanner, or other input/output devices described herein.

Still referring to FIG. 1, the partner computing systems 112 may be managed by third-party partners (e.g., the FDA, the EHA, Health Canada, partner company 1, partner company 2, partner computing system xyz, etc.) and can be or include a computing device or system configured to communicate with the provider computing system 104 over the network 118. For instance, the partner computing systems 112 can be a server computer system, a gateway computing system, a laptop computer a desktop computer, and any other network-connected device that can communicate over the network 118. For example, one of the partner computing systems 112 may be the Electronics Submission Gateway (ESG) of the FDA through which one or more E2B XML files may be received from and/or provided to. In another example, one of the partner computing systems 112 may include a laptop computer operated by an employee of a partner company. In another example, one of the partner computing systems 112 may include a study computer system including unblinded medical product data.

In operation, the partner computing systems 112 may communicate with the provider computing system 104 or the client computing device 108 to send and/or receive one or more electronic communications (e.g., case datasets, source files, unblinded medical product data, etc.). For instance, a customer (e.g., pharma company 123) may submit case datasets to the FDA over the ESG of the FDA. Accordingly, the provider computing system 104 may provide case datasets to the first partner computing system associated with the FDA. For instance, the provider computing system 104 may generate an outbound transmission including one or more case datasets. Then, the provider computing system 104 may output the outbound transmission to the first partner computing system 112. In another example, a client computing device 108 may generate a request to unblind blinded medical product data. The request may include authentication data. Then, the provider computing system 104 may generate a request for unblinded medical product data including the authentication data and provide the request to one of the partner computing systems 112. The partner computing system 104 may authenticate the authentication data and provide the unblinded medical product data to the provider computing system 104.

As shown, each partner computing system 112 includes a network interface 176, a processing circuit 176, and a partner repository 180. In some embodiments, each partner computing system 112 further includes a key repository (not shown) for storing AS2 keys and certificates.

The network interface 176 is structured to establish connections with the provider computing system 104 by way of the network 118. The network interface 176 includes program logic and/or hardware-based components that connect the client computing device 108 to the network 118. For example, the network interface 176 may include any combination of a wireless network transceiver (e.g., a cellular modem, a broadband modem, a Bluetooth transceiver, a Wi-Fi transceiver, a Li-Fi transceiver, etc.) and/or a wired network transceiver (e.g., an Ethernet transceiver). In some embodiments, the network interface 176 includes the hardware and machine-readable media structured to support communication over multiple channels of data communication (e.g., wireless, Bluetooth, near-field communication (NFC). In some embodiments, the network interface 176 may include AS2 Gateway logic (similar to the AS2 Gateway logic 127). In some embodiments, the network interface 176 includes cryptography logic and capabilities to establish a secure communications session.

The processing circuit 178, as shown, comprises a memory 182 and a processor 184. The memory 182 includes one or more memory devices (e.g., RAM, NVRAM, ROM, flash memory, hard disk storage, etc.) that store data and/or computer code for facilitating the various processes described herein. That is, in operation and use, the memory 182 stores at least portions of instructions and data for execution by the processor 184 to control the processing circuit 178. The memory 182 may be or include tangible, non-transient volatile memory and/or non-volatile memory. The processor 184 may be implemented as a general-purpose processor, an application specific integrated circuit (ASIC), one or more field programmable gate array (FPGAs), a digital signal processor (DSP), a group of processing components or other suitable electronic processing components.

Likewise, the partner repository 180 may be repository (e.g., a database) that is structured or configured to receive, store, and manage partner data (e.g., partner case datasets, partner unblinded medical product data, source files, etc.).

For example, the partner repository 180 may receive case datasets and related case objects and store the case datasets therein. In another example, the partner repository 180 may receive unblinded medical product data. Then, in response to receiving a query or a request for the unblinded medical product data, the partner repository 180 may provide and/or return the unblinded medical product data stored therein that matches the query or request. Accordingly, the partner repository 180 can be structured according to various database types, such as, relational, hierarchical, network, flat, point-in time, and/or object relational. In some embodiments, the case partner repository 180 includes a plurality of nonvolatile/non-transitory storage media such as solid-state storage media, hard disk storage media, virtual storage media, cloud-based storage drives, storage servers, and/or the like.

Figure 2:
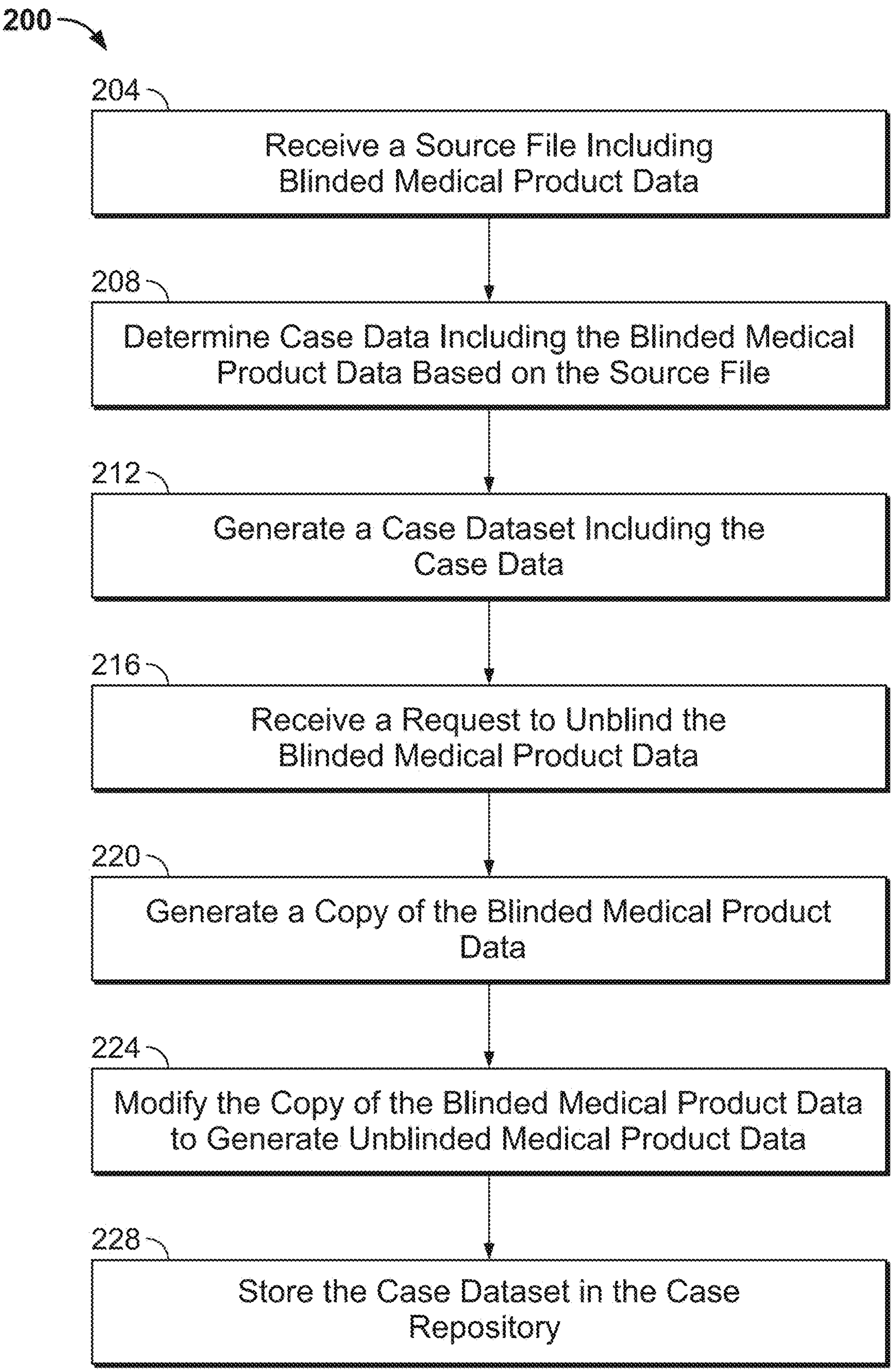
FIG. 2 may be a flow diagram of a method for generating a case dataset, according to an example embodiment.

Referring now to FIG. 2, a method 200 of generating a case dataset is shown, according to an example embodiment. Method 200 can be carried out by the system of FIG. 1. More particularly, the method 200 can be carried out by the processing circuit 128 of the provider computing system 104 and through communication with the client computing devices 108 and the partner computing systems 112.

Method 200 commences at step 204 at which the provider computing system 104 receives a source file including adverse event data. The source file and the adverse event data may be associated with one or more adverse events. For instance, the source file may include adverse event information for each adverse event. Further, the source file may be received from one of the client computing devices 108 or one of the partner computing systems 112. In some embodiments, the source file may be an E2B (R2 or R3) XML file received via an AS2 Gateway communication from the one of the partner computing systems 112 or the client computing devices 108. In other embodiments, the source file may be received from one of the partner computing systems 112 via an application programming interface (API) of the provider computing system 104. In other embodiments, the source file may be at least one of a PDF file, an Excel file, a CSV file, a web form, an email, or other file types described herein. The adverse event data may identify or include medical product or substance data (e.g., a substance name, a medical product slang name or term, a medical product trade name, a NDC, a medical product identifier, a dosage, a country of origin, a strength, a lot number, a route of administration, etc.), study data (e.g., a study identifier), an adverse event term and code (e.g., a MedDRA term and code), reporter data (e.g., a reporter name, a reporter country, a reporter address or contact information (e.g., email, phone number, IP address, FTP address, etc.)), patient data (e.g., patient initials, patient address or contact information), a report type (e.g., spontaneous, from study, from marketed medical product, etc.), a seriousness of the adverse event, and the like.

In some embodiments, the adverse event data includes blinded medical product data and associated study data. For instance, a patient in a blind-protected clinical trial may experience an adverse event after taking a potential medical product (e.g., a medical product being tested, a comparator, a placebo, etc.). The adverse event may be recorded and submitted in a source file to the provider computing system 104. In the source file, the medical product data may be blinded. For instance, in place of a medical product name, the blinded medical product data may include the name of the study. In another example, in place of a dosage, the blinded medical product data may include a token.

In some embodiments, the adverse event data may include unblinded medical product data (also referred to as medical product data) and a blind field indicating the medical product data is to be blinded. In response, at or after step 204, the provider computing system 104 may modify the medical product data to generate blinded medical product data. For instance, as described herein, the provider computing system 104 may tokenize the medical product data to generate blinded medical product data. The blinded medical product data may be utilized, by the provider computing system 104 in the method 200, and the unblinded medical product data may be stored in a medical product repository (not shown). In another example, the provider computing system 104 may encrypt the medical product data to generate blinded medical product data.

Once the provider computing system 104 has received the source file, the method 200 proceeds to step 208 at which the provider computing system 104 determines or generates case data based on the source file. In some embodiments, the provider computing system 104 may determine the case data based at least partially on the adverse event data. For instance, the provider computing system 104 may transform or add each piece of adverse event data to a specific record or field of the case data. In one example, an adverse event term of the adverse event data may be added to an adverse event field of the case data. In this regard, the case data may include at least a portion of the adverse event data of the source file. In another example, the provider computing system 104 may determine at least a portion of the case data by transforming adverse event data that is in an incorrect format into a correct format (e.g., "SE" to "Sweden"). In some embodiments, at step 208, the provider computing system 104 may further generate a priority of the case based on the adverse event data, a rank of the adverse events associated with the current case, a rank of the medical products, and the like.

Additionally, to determine case data at step 208, the provider computing system 104 may generate the medical product data of the case data to include the blinded medical product data. For instance, the case data may include a case medical product data record. Then, for each of the fields of the case medical product data record, the provider computing system 104 may utilize the blinded medical product data (e.g., the blinded medical product name, the blinded medical product identifier, the blinded medical product dosage, etc.).

Once the provider computing system 104 has determined the case data based on the source file, the method 200 proceeds to step 212 at which the provider computing system 104 generates a case dataset including the case data. In some embodiments, at step 212, the provider computing system 104 may generate a case data object (also referred to as a data record) associated with or including the case identifier of the case. In this regard, the case dataset may include a case data object which may be used as a vehicle or apparatus for the case dataset and storing the case data within the case repository 133 of the provider computing system 104. For instance, the provider computing system 104 may determine or generate the case data and then populate the case data object with the case data.

In some embodiments, before steps 208 or 212, the provider computing system 104 may search the case repository 133 for potential duplicate case datasets of the case dataset to be generated. For instance, the provider computing system 104 may search the case repository 133 for cases that include a similar or the same case identifier, medical product(s), adverse event(s), report date, reporter name, and the like. In response to returning one or more potential duplicate case datasets, the provider computing system 104 may provide the potential duplicate case datasets and the adverse event data of the source file (or the newly generated case data) for review and comparison. Then, in response to receiving an indication the case datasets are not duplicates, the provider computing system 104 may proceed to step 208 or 212.

In some embodiments, after step 212, the provider computing system 104 may store the case dataset (e.g., as a case data object) in the case repository 133. For instance, the provider computing system 104 may add or provide the case dataset to the case repository 133 for storage therein.

Once the provider computing system has generated the case dataset, the method 200 proceeds to step 216 at which the provider computing system 104 receives a request to unblind the blinded medical product data of the case dataset. As described herein, a customer may unblind blinded medical product data, to determine the reportability of the case dataset. For instance, a case dataset may be determined to be a Serious Unexpected Suspected Adverse Event (SUSAR), which typically is reported to a health authority. However, before determining reportability, the customer may need to know which, if any, medical product was suspected of causing the adverse event. Accordingly, one of the client computing devices 108 may generate a request to unblind the medical product data. In some embodiments, the request may include authentication data. In some embodiments, the request may include unblinded medical product data.

In some embodiments, at or after step 216, the provider computing system 104 may determine if the client computing device 108 has unblinded data privileges. For instance, the provider computing system 104 may determine if the account associated with the client computing device 112, which provided the request, has unblinded data privileges. In response to the provider computing system 104 determining the client computing device 108 has unblinded data privileges, the provider computing system 104 may proceed to step 220 of the method 200. In comparison, in response to the provider computing system 104 determining the client computing device 108 does not have unblinded data privileges, the method 200 may end.

Once the provider computing system 104 has received the request to unblind the blinded medical product data, the method 200 proceeds to step 220 at which the provider computing system 104 generates a copy of the blinded medical product data. As described herein, the blinded medical product data may be stored in a medical product data record of the case data. Accordingly, the provider computing system 104 may generate a copy or reproduction of the medical product data record of the case data (also referred to as a second medical product data record).

Once the provider computing system 104 has generated the copy of the blinded medical product data, the method 200 proceeds to step 224 at which the provider computing system 104 modifies the copy of the blinded medical product data to generate or determine unblinded medical product data. For instance, as described herein, the provider computing system 104 may generate a request for unblinded medical product data including the received authentication data, and provide the request to one of the partner computing systems 112. Then, in response to receiving the unblinded medical product data, the provider computing system 104 may modify the second medical product data record to include the unblinded medical product data. In another example, the provider computing system 104 may generate a request for unblinded medical product data, and provide the request to one of the client computing devices 108 (e.g., the client computing device 108 from which the request to unblind the medical product data was received). Then, in response to receiving the unblinded medical product data, the provider computing system 104 may modify the second medical product data record to include the unblinded medical product data. In another example, the provider computing system 104 may provide the tokenized medical product data to the medical product repository (not shown). The medical product repository may determine the unblinded medical product data associated with the tokenized medical product data and return the unblinded medical product data. Then, the provider computing system 104 may modify the second medical product data record to include the unblinded medical product data. In another example, the provider computing system 104 may decrypt the encrypted medical product data to determine unblinded medical product data. Then, the provider computing system 104 may modify the second medical product data record to include the unblinded medical product data.

In some embodiments, at or after step 224, the provider computing system 104 may add the unblinded medical product data (e.g., the second medical product data record) to the case data and the case dataset. For instance, the provider computing system 104 may add the second medical product data record such that the case data of the case dataset includes a first (blinded) medical product data record and a second (unblinded) medical product data record.

By generating a copy of the blinded medical product data and then unblinding the copy of the blinded medical product data, the present systems and methods provide for isolation between the unblinded/unmasked medical product data and the blinded/masked medical product data and thereby provide for improved data security. For instance, because the systems and methods generate a copy of the blinded medical product data and then unblind the copy of the blinded medical product data, the present system and methods create two, isolated, sets of medical product data: one masked and one unmasked, which provides for an improvement to data security. For instance, by isolating masked data, the present systems and methods limit the amount of sensitive data an attacker can access if they breach a system's defenses. Even if they gain access to the masked data, it's useless without the key to unmask it. This compartmentalization minimizes potential data theft. Likewise, by controlling access to unmasked data through the case access groups, the present systems provide for stricter privilege levels. Only authorized or privileged users with a legitimate need would have access to the unmasking process. This reduces the risk of accidental exposure or unauthorized access. Furthermore, because the present systems and methods maintain data integrity by keeping a copy of the blinded or masked medical product data and the unblinded or unmasked medical product data, specific user's (e.g., those who do not have unmasked data privileges) can leverage masked data sets, reducing the need for the use and disclosure of sensitive data. This minimizes security risks during the case dataset generation and intake process.

Additionally, by generating a copy of the blinded medical product data and then unblinding the copy of the blinded medical product data, the present systems and methods keep a store of the blinded medical product data and the unblinded medical product data, and thereby provide for improved data integrity. For instance, by isolating blinded medical product data from unblinded medical product data, the present systems and methods create separation between the masked data and the original unmasked data. This separation minimizes the chance of accidentally modifying or corrupting the sensitive data during processing or storage. Likewise, because the masked medical product data is stored independently of the unmasked medical product data, the present systems and methods track and monitor changes to the masked medical product data more easily, thereby identifying any unauthorized access or manipulation attempts and making it easier to maintain an audit trail for data integrity purposes.

Once the provider computing system 104 has modified the blinded medical product data to generate or determine unblinded medical product data, the method 200 proceeds to step 228 at which the provider computing system 104 stores the case dataset (e.g., as a case data object) in the case repository 133. For instance, the provider computing system 104 may add or provide the case dataset to the case repository 133 for storage therein.

In some embodiments, after step 228, the provider computing system 104 may receive a request to determine electronic transmissions associated with the case dataset from one or more of the client computing devices 108. In some embodiments, the provider computing system 104 may automatically determine electronic transmissions after step 228 (i.e., without receiving a request to do so).

In some embodiments, after step 228, the provider computing system 104 may output the case dataset including at least a portion of the case data based on the case dataset, and/or received submission rules data. In this regard, the provider computing system 104 may generate a transmission including the case dataset including at least a portion of the case data (e.g., the blinded medical product data and/or the unblinded medical product data). In some embodiments, the provider computing system 104 may receive submission rules data indicating which portions of the case data are to be output, based on the specific destination address or partner computing system 112 to which the case dataset is to be output. For instance, the provider computing system 104 may output the case dataset including the blinded case data to a first partner computing system 112 associated with a first destination address (e.g., email123@gmail.com). In another example, the provider computing system 104 may output the case dataset including the unblinded case data to a second partner computing system 112 associated with a second destination address (e.g., FTP address 1232342423).

In some embodiments, to generate the electronic transmission and/or output the case dataset, the provider computing system 104 may determine if the case dataset meets or fulfills the selected submission rules of the submission rules data. For instance, the provider computing system 104 may select a submission ruleset (and the associated portions of submission rules data) from the submission rules repository (not shown). Next, the provider computing system 104 may select or filter the two submission rulesets (and their associated portions of submission rules data) to three submission rules (e.g., a first submission rule for serious case datasets that are associated with the FDA and the medical product type "Drugs," a second submission rule for serious case datasets that are associated with the EMA and the medical product type "OTC Drugs," and a third submission rule for serious case datasets that are associated with the EMA and unexpected) based on the three submission rules matching the case dataset. In this example, the three submission rules match the case dataset because the case dataset is for a medical product that is registered with the FDA (e.g., includes a medical product registration associated with the selected portion of the medical product registration data) as a drug and the EMA as an OTC Drug and because the case dataset includes a seriousness of serious and an expectedness of unexpected. Accordingly, in response to the case dataset meeting or fulfilling the submission rule, the provider computing system 104 may generate an electronic transmission and output the case dataset.

Figure 3:
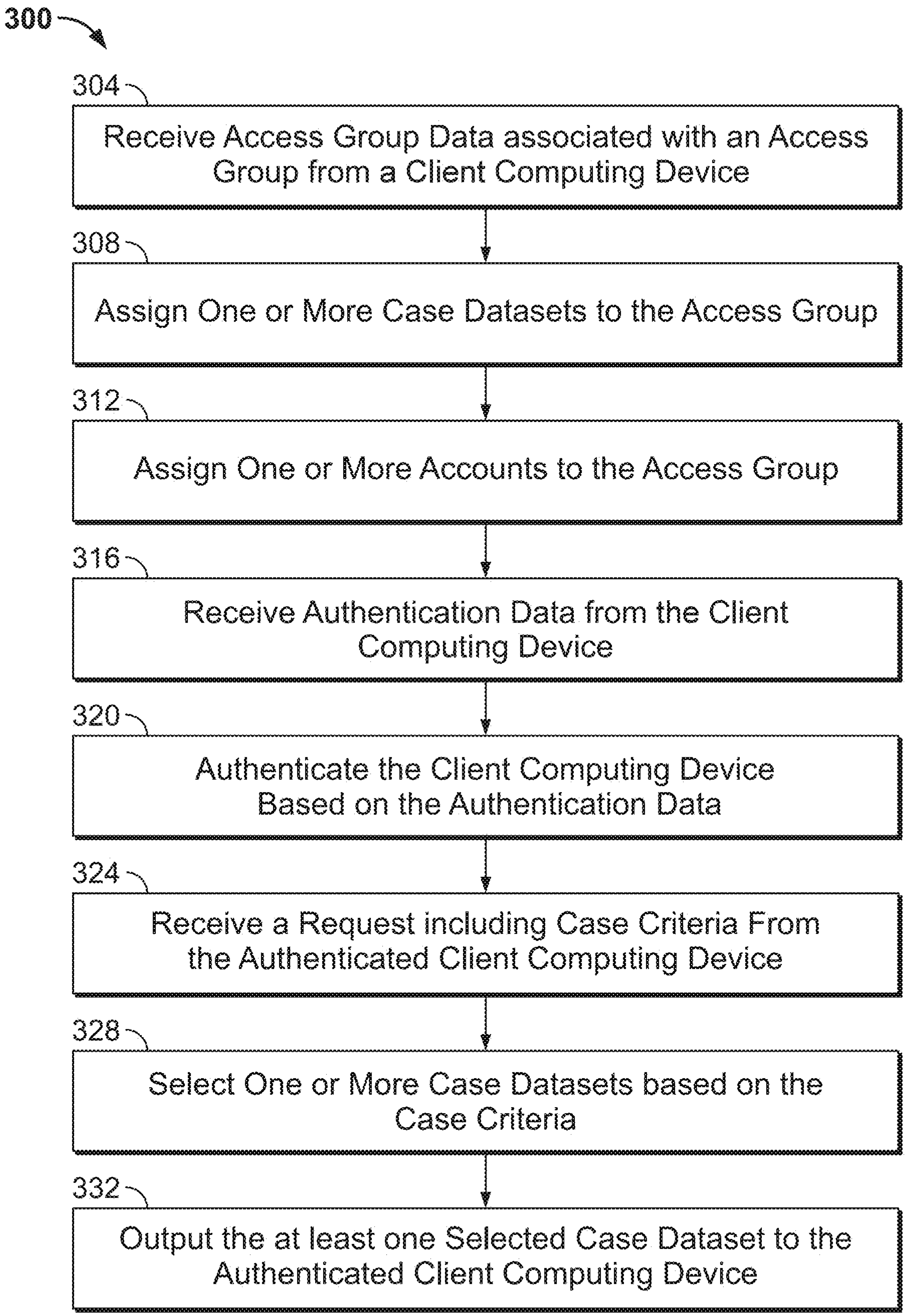
FIG. 3 may be a flow diagram of a method for accessing one or more case datasets via a case access group, according to an example embodiment.

Referring now to FIG. 3, a method 300 of accessing one or more case datasets via a case access group is shown, according to an example embodiment. While different overall, it should be understood that any steps or discussion of the method 300 may be applied or included within the method 200, and vice versa, and that such combinations are included within the scope of the present disclosure. For example, the method 200 may include any of the steps 304-332, after or before any steps included in the method 200, and the method 300 may include any of the steps 204-228, after or before any of the steps included in the method 300. In one specific example, at or before step 216, the provider computing system 104 may perform steps 304-320 of the method 300. Then, in response to authenticating the client computing device 108, the provider computing system 104 may determine if the authenticated client computing device 108 has blind access privileges. For instance, the provider computing system 104 may determine if the account associated with the authenticated client computing device 108 has blind access privileges by searching or querying the account repository 132 for the account. In response to the account having blind access privileges, the method 200 may proceed to step 220. In response to the account not having blind access privileges, the method 200 may end. In some embodiments, the provider computing system 104 may determine if the account associated with the authenticated client computing device 108 has or includes unblinding privileges.

Method 300 can be carried out by the system of FIG. 1. More particularly, the method 300 can be carried out by the processing circuit 128 of the provider computing system 104 and through communication with the client computing devices 108 and the partner computing systems 112.

Method 300 commences at step 304 at which the provider computing system 104 receives (case) access group data, which may be associated with one or more access groups. The access group data may include case assignment data or rules and user assignment data, which will be described further herein. In some embodiments, the access group data may include blinded access privileges or data and/or PII access privileges or data that indicate whether the access group has access to blinded case data and PII case data, respectfully. In other embodiments, the blinded access privileges and the PII access privileges may be account specific and included in the user assignment data. In some embodiments, the access group data is received in a request to generate a new access group. In other embodiments, the access group data is received in a request to alter an existing access group.

In some embodiments, the access group data is received from one of the client computing devices 108. In some embodiments, the access group data is received from a client computing device 108 associated with an account having administrator (admin) privileges. For instance, prior to step 304, the client computing device 108 may provide authentication data to the provider computing system 104. In response, the provider computing system 104 may search or query the account repository 132 for the authentication data and find matching authentication data (e.g., authentication data that matches the received authentication data). Further, the authentication data returned from the account repository 132 may be associated with administrator credentials or an admin user and have administrative privileges (e.g., authorization to generate, manage, and delete case access groups and their associated data).

In some embodiments, after receiving the access group data, the provider computing system 104 may generate the access group and/or an access group data object. For instance, if the access group data is received in a request to generate a new access group, the provider computing system 104 may generate an access group and/or an access group data object including the case assignment data and the user assignment data. In some embodiments, after receiving the access group data, the provider computing system 104 may select or query the access group from the account repository 132 or the access group repository (not shown). For instance, if the access group data is received in a request to modify or alter an existing access group, the provider computing system 104 may search the account repository 132 for the access group and/or an access group data object. Then, the provider computing system 104 may update the access group and/or the access group data object to include the case assignment data or the user assignment data of the request.

In some embodiments, prior to step 304, the provider computing system 104 may receive case access group preferences (also referred to as blind preferences and PII preferences) from one of the client computing devices 108. The case access group preferences will be described further herein, but may specify which fields or pieces of case data are to be masked or hidden in response to an account not having the blind or PII privileges. In some embodiments, after receiving the case access group preferences, the provider computing system 104 may store them in the account repository 132 or the access group repository (not shown).

Once the provider computing system 104 has received the access group data, the method 300 proceeds to step 308 at which the provider computing system 104 assigns one or more case datasets to the access group. As described herein, the access group data may include case assignment data or rules which may specify the criteria for a case dataset to be assigned to the access group. For instance, the case assignment data may indicate a case dataset is to be assigned to the access group if it originated or is to be reported in a specific country or jurisdiction (e.g., the USA), if it is associated with a medical product in a clinical study (e.g., is a study case), if it is associated with a marketed medical product (e.g., is a marketed case), based on the sponsor or customer of the case, based on the state (e.g., open, closed, submitted, medical review, etc.) of the case, based on the medical product of the case, based on the seriousness of the case (e.g., serious-resulted in death, non-serious, serious-birth defect, etc.), and based on other case data. For example, the case assignment data may indicate a case dataset is to be assigned to the access group ("Europe-Study"), in response to the case dataset originating or being reported in Europe and the case dataset including or being associated with a medical product that is undergoing a clinical study. In another example, the case assignment data may indicate a case dataset is to be assigned to the access group ("Worldwide-Marketed"), in response to the case dataset being reported in multiple countries worldwide and the case dataset including or being associated with a medical product that is currently marketed. While these are a few examples, it should be understood that many combinations of case data may be utilized and indicated in the case assignment data, and that such combinations are within the scope of the present disclosure.

In some embodiments, to assign each case to the access group, the provider computing system 104 (and more particularly the access group generation and management circuit 144) may search or query the case repository 134 for each case dataset that matches or meets the case assignment data or rules. For instance, using the ("Europe-Study") example above, the provider computing system 104 may search or query the case repository 134 for each case dataset that was reported or originated in Europe and is associated with or includes a medical product that is undergoing a clinical study. In response, the case repository 134 may return each matching case dataset and/or case dataset data object. The provider computing system 104 may then add the case access group to the case data of the case dataset or the case dataset data object. For instance, the provider computing system 104 may add a reference or an association (e.g., a link, a reference pointer, a name) to the access group in the case dataset data object, and then store the updated case dataset and/or case dataset data object in the case repository 134. The reference will be described further herein, but may be used when determining which case dataset(s) to return to a specific user. In other embodiments, the provider computing system 104 may add reference or an association (e.g., a link, a reference pointer, a name) for each returned case dataset (from the case repository 134) to the case access group data or a case access group data object, and then store the case access group and/or the case access group in the case repository 134.

Once the provider computing system 104 has assigned one or more case datasets to the access group, the method 300 proceeds to step 312 at which the provider computing system 104 assigns one or more accounts or users to the access group. As described herein, the access group data may include user assignment data or rules which may specify the user accounts or the criteria for an account to be assigned to the access group. For instance, the user assignment data may indicate a user's account is to be assigned to the access group if they have a specific title (e.g., case processor-USA, CSO, CEO, head or research, medical reviewer, etc.), or if they work in a specific location or office (e.g., North Carolina, USA; UK, Europe, Japan, Asia; etc.). In another example, the user assignment data may include or specify specific accounts (e.g., usernames, names, emails, etc.) which are to be assigned to the access group.

In some embodiments, to assign each user or account to the access group, the provider computing system 104 (and more particularly the access group generation and management circuit 144) may search or query the account repository 132 for each account that includes one of the users identified in the user assignment data. In response, the account repository 132 may return each matching account and/or account data object. The provider computing system 104 may then add the case access group to the account data of the account. For instance, the provider computing system 104 may add a reference or an association (e.g., a link, a reference pointer, a name) to the case access group in the account or the account data object, and then store the updated account data and/or account data object in the account repository 132. In other embodiments, the provider computing system 104 may add reference or an association (e.g., a link, a reference pointer, a name) for each returned account (from the account repository 132) to the case access group data or a case access group data object, and then store the account or the account data object in the account repository 132.

In some embodiments, the user assignment data may further include or specify blind access privileges, unblind privileges, and/or PII access privileges for each specific account or user. The blind access privileges may be used in determining if the account has access to specific unblinded case data. As described herein, case data may be blinded in clinical studies or trials to blindly determine the effect a medical product has when compared to a placebo or another medical product. In this regard, to prevent bias, the patient and other people associated with the clinical study (e.g., the prescribing physician, case processors, etc.) may be unaware of which product (e.g., the medical product, the placebo, another medical product) was provided to the patient. In this regard, the case data may include multiple fields or portions (e.g., medical product name, medical product dosage, medical product substance(s), etc.) that are blinded or masked to specific accounts. For example, an account with blind access privileges may see the medical product name "Placebo;" whereas, an account with no blind access privileges may see the medical product name "****" or "Blinded" or "xxxxx." Similarly, the unblind privileges may be used in determining if the account has permission to unblind blinded medical product.

Likewise, the PII access privileges may be used in determining if the account has access to specific PII. As described herein, case data may include personally identifying information or data of patients that is private and protected by the law (e.g., the Health Insurance Portability and Accountability Act (HIPAA)). Accordingly, to protect the patient and their privacy, only specific accounts or users may have access to the PII, while the PII is masked or hidden to other specific accounts. For example, an account with PII access privileges may see the name "John Smith" or the address 111 Address St., Milwaukee WI, 53209; whereas, an account with no blind access privileges may see the name "**" or "J.S." or "xxxxx" and the address "" or "xxxxx". In some embodiments, the provider computing system 104** may add the blind access privileges and the PII access privileges for each specific account to the account data as part of assigning the account to the access group.

Once the provider computing system 104 has assigned one or more accounts to the access group, the method 300 proceeds to step 316 at which the provider computing system 104 receives authentication data (also referred to as client computing device authentication data) from one of the client computing devices 108. As described herein, the authentication data may be or include a username, a password, a one-time use key, a two-factor authentication code, and/or an electronic address (e.g., IP address, email address, FTP address, network address, etc.). For example, a user of the client computing device 108 may wish to access one or more case datasets of the provider computing system 104 and begin a log-in process. Accordingly, via the network 118, the client computing device 108 may access a specific Uniform Resource Locator (URL) associated with the provider computing system 104 and be prompted with a log-in page (not shown) by providing a request to access the URL with the IP address of the client computing device 108. The log-in page may request authentication data of an account previously set up by the user or the user's employer. Then, via the log-in page, the user of the client computing device 108 may provide their authentication data, which may then be provided, by the respective client computing device 108, to the provider computing system 104. In one example, the user may provide a username (e.g., an email address) and matching password. In response, the provider computing system 104 may request a two-factor authentication code and provide the two-factor authentication code to the user (e.g., at an electronic address of the client computing device 108, at a phone number of the user, at an email address of the user, etc.). The user of the client computing device 108 may receive the two-factor authentication code, and provide it to the provider computing system 104 via the log-in page. In this way, the provider computing system 104 may receive authentication data including the IP address of the client computing device 108, the username, the password, and the two-factor authentication code of the user.

Once the provider computing system 104 has received the authentication data, the method 300 proceeds to step 320 at which the provider computing system 104 authenticates the client computing device 108 based on the authentication data. To authenticate the specific client computing device 108 and/or the authentication data, the provider computing system 104 may search the account repository 132 for an account including authentication data that matches the received authentication data. For instance, the provider computing system 104 may query or search the account repository 132 for a username that matches the username of the received authentication data (e.g., john.smith@company123.com). Then, in response to returning a matching account, the provider computing system 104 may determine the password matches a password of the matching account. Further, the provider computing system 104 may determine the two-factor authentication code matches the two-factor authentication code provided to the user. Then, in response to each piece of authentication data matching that stored in the account repository 132, the provider computing system 104 may determine the client computing device 108 is authenticated.

In some embodiments, in response to authenticating the client computing device 108, the provider computing system 104 may provide a limited-use key (LUK) (e.g., of a key repository (not shown)) to the client computing device 108. Further, the provider computing system 104 may add a LUK-account pair to the account repository 132, the key repository (not shown), and/or LUK lookup table which may indicate the LUK is associated with the authenticated account for which the client computing device 108 provided authentication data. In this regard, for a limited time (e.g., one hour, two hours, four hours, one day, etc.) the client computing device 108 may provide the LUK along with any requests, and the provider computing system 104 may determine the request is coming from the authenticated account of the client computing device 108, based on the LUK. In other embodiments, in response to authenticating the client computing device 108, the provider computing system 104 may add the electronic (also referred to as sender) address (e.g., the IP address, the domain name, etc.) of the client computing device 108 to the account repository 132 or an electronic address lookup table which may indicate the electronic address is associated with the authenticated account for which the client computing device 108 provided authentication data. In this regard, for a limited time (e.g., one hour, two hours, four hours, one day, etc.) the client computing device 108 may provide requests from the electronic address, and the provider computing system 104 may determine the request is coming from the authenticated account of the client computing device 108, based on the electronic address.

Once the provider computing system 104 has authenticated the client computing device 108 based on the authentication data, the method 300 proceeds to step 324 at which the provider computing system 104 receives a request for one or more case datasets including case criteria or case search criteria from one of the client computing devices 108. The request may be received from the authenticated client computing device 108. In some embodiments, the request may further include a LUK or a sender address. For instance, the provider computing system 104 may receive the request including the case criteria and a LUK from one of the client computing devices 108. In response, the provider computing system 104 may look up or search the LUK in the LUK lookup table and determine the LUK is associated with a specific account of the account repository 132 and that the client computing device 108 is authenticated. In another example, the provider computing system 104 may receive the request including the case criteria and a sender address (e.g., an IP address) from one of the client computing devices 108. In response, the provider computing system 104 may look up or search the sender address in the electronic address lookup table and determine the electronic address is associated with a specific account of the account repository 132 and that the client computing device 108 is authenticated.

In some embodiments, at or after steps 320 or 324, the provider computing system 104 may determine the case access group of the client computing device 108. For instance, as a part of authenticating the client computing device 108 at step 320, the provider computing system 104 may further determine the case access group of the authenticated account. As described herein, the case access group for the account may be stored in the account data or the account data object. Accordingly, while authenticating the account of the client computing device 108, the provider computing system 104 may further associate the case access group of the account with the LUK or the electronic address. In other embodiments, in response to receiving the request including the case criteria, the provider computing system 104 may search the account repository 132 for the account matching the LUK and determine the case access group of the account. In this regard, prior to step 328, the provider computing system 104 may determine the case access group of the account.

Once the provider computing system 104 has received the request including the case criteria, the method 200 proceeds to step 328 at which the provider computing system 104 selects one or more case datasets based on the case criteria. As described herein, the provider computing system (and more particularly, the case intake and management circuit 148) may select the case datasets from the case repository 134 based on the case criteria. The case criteria may include or specify one or more fields of the case data. For instance, the case criteria may identify a specific medical product (e.g., a medical product identifier (e.g., a national drug code (NDC)), a specific medical code, a date or set of dates within which the case was generated or received, a specific country of origin, and the like. In this regard, the provider computing system 104 may search the case repository 134 for case datasets that match the case criteria of the request and receive or select the matching case datasets, in response.

In some embodiments, at step 328, the provider computing system 104 may select one or more case datasets from the case repository 134 based on the case criteria and the case access group of the authenticated account. For instance, as described herein, at step 308, each case dataset may be assigned to one or more case access groups. Accordingly, at step 328, the provider computing system 104 may search the case repository 134 for cases that match the case criteria (e.g., include case data that matches the case criteria) and that are in the case access group of the authenticated account. For example, an account may be assigned the case access group (US-Marketed) and therefore have access to case datasets that are for marketed medical products and originated in the US. Additionally, based on the case assignment data of the case access group, multiple case datasets may be assigned to the same case access group (US-Marketed). Then, at step 328, the provider computing system 104 may search for case datasets that are assigned to the case access group (US-Marketed) and match or meet the case criteria (e.g., include a specific medical product code).

Once the provider computing system 104 has selected the one or more case datasets from the case repository 134, the method 200 proceeds to step 332 at which the provider computing system 104 outputs the one or more case datasets to the authenticated client computing device 108. The one or more selected case datasets may be output in response to the request and based on the authentication data (e.g., based on the LUK of the request, etc.). In some embodiments, the one or more case datasets may be output to the client computing device 108 via a user interface and a case page 400, as will be described further herein. In other embodiments, the one or more case datasets may be output as an E2B R2 or R3 (XML) file and via the AS2 communication protocol. In other embodiments, the one or more case datasets may be output as an email to the electronic address (e.g., email address) of the authenticated client computing device 108.

In some embodiments, prior to step 332 (e.g., at step 328, after step 328, etc.), the provider computing system 104 may select the portions of the case dataset to output based on the blind access privileges and the PII access privileges of the authenticated account. For instance, as described herein, the case dataset may include blinded medical product data (e.g., a first (blinded) medical product record) and unblinded medical product data (e.g., a second (unblinded medical product record)). Accordingly, for accounts with blind access privileges, the provider computing system 104 may output the case dataset including the blinded medical product data and the unblinded medical product data. In comparison, for accounts without blind access privileges, the provider computing system 104 may output the case dataset including the blinded medical product data but not the unblinded medical product data.

In other embodiment, the provider computing system 104 may modify the one or more case datasets based on the blind access privileges and the PII access privileges of the authenticated account. For instance, as described herein, each account may or may not have blind access privileges and/or PII access privileges. Accordingly, if an account does not have blind access privileges (and the case is a blinded case (e.g., is identified as a blinded case), the provider computing system 104, prior to step 228, may modify each of the one or more case datasets to remove the unblinded medical product data (e.g., the medical product of the case, medical product registrations, substances of the medical product, etc.). In comparison, if the respective case is not a blinded case (e.g., is not identified as a blinded case) or the account has blind access privileges, the provider computing system 104 may not modify the case dataset. Likewise, if an account does not have PII access privileges, the provider computing system 104, prior to step 228, may modify each of the one or more case datasets to mask or hide any PII data (e.g., the patient's name, date of birth, address, etc.). In comparison, if the account has PII access privileges, the provider computing system 104 may not modify each case dataset. In some embodiments, to mask or hide the blinded case data and the PII case data, the provider computing system 104 may blind or mask the fields specified by the case access group preferences described herein.

It should be understood that while steps 316-332 are each described with reference to a single client computing device 108, steps 316-332 may take place with multiple client computing devices 108, as is typical for multi-tenant systems. For instance, steps 316-332 may be associated with and performed with two, three, four, (and so on) client computing devices 108. Each client computing device 108 may have separate authentication data (e.g., a separate username and password) and be included in or a part of one or more case access groups. In one example, two sets of authentication data may be associated with the same access group. In another example, two sets of authentication data may be associated with different access groups.

In one specific example, steps 316-332 may be performed for two, separate, client computing devices 108. For example, at step 316, the provider computing system 104 may receive first authentication data (e.g., a first username and password) from a first client computing device 108 and second authentication data (e.g., a second username and password, which is different or not the same as the first username and password) from a second client computing device 108. Then, at step 320, the provider computing system 104 may authenticate the first client computing device based on the first authentication data and the second client computing device based on the second authentication data. Further, at or after step 320, the provider computing system 104 may determine the first authentication data is for or a part of a first account which is included in a first access group, and the second authentication data is for or a part of a second account which is included in a second access group, which is different from the first access group. Then, at step 324, the provider computing system 104 may receive a first request including first case criteria from the first client computing device 108 and a second request including second case criteria from the second client computing device 108. The first case criteria and the second case criteria may be the same. At step 328, the provider computing system 104 may select two or more first case datasets based on the first case criteria, in response to the first request; and may select two or more second case datasets based on the second case criteria. In some embodiments, depending on the tier of the permissions and the case assignment data, at least one of the first case datasets may be the same as at least one of the second case datasets; and at least one of the first case datasets may be different from (i.e., is not included in) the second case datasets. In some embodiments, depending on the tier of the permissions and the case assignment data, the first case datasets may be entirely different from the second case datasets (i.e., not one first case dataset is the same as any of the second case datasets). At step 332, the provider computing system 104 may output the first case datasets to the authenticated first client computing device 108 and the second case datasets to the authenticated second suer computing device 108.

Referring now to FIGS. 4A-5C, user interfaces shown and displayed to the user of the one or more client computing devices 108 during the methods 200 and/or 300 are shown, according to example embodiments. As described herein, the user interfaces of FIGS. 4A-5C may be one or more of web interfaces generated by the provider computing system 104 and rendered by each of the client computing devices 108 as part of a web application or graphical user interfaces downloaded and generated by each of the client computing devices as part of a software application (e.g., a mobile application, etc.). Further, the user interfaces shown on FIGS. 4A-5C allow for communication between the user and the provider computing system 104 via the respective client computing device 108 (specifically via the I/O circuit 162). Through interaction with the various user interfaces, the user may provide user input, feedback, and other data requested by the provider computing system 104. In this regard, it should be understood that each interaction described herein by the user with the user interfaces of FIGS. 4A-5C may be provided to one or more of the client computing devices 108 and then transmitted to the provider computing system 104 and that each action described herein as occurring to the respective client computing device 108 (e.g., navigating to a certain page, generating a popup, etc.) may be performed by the provider computing system 104.

Figure 4A:
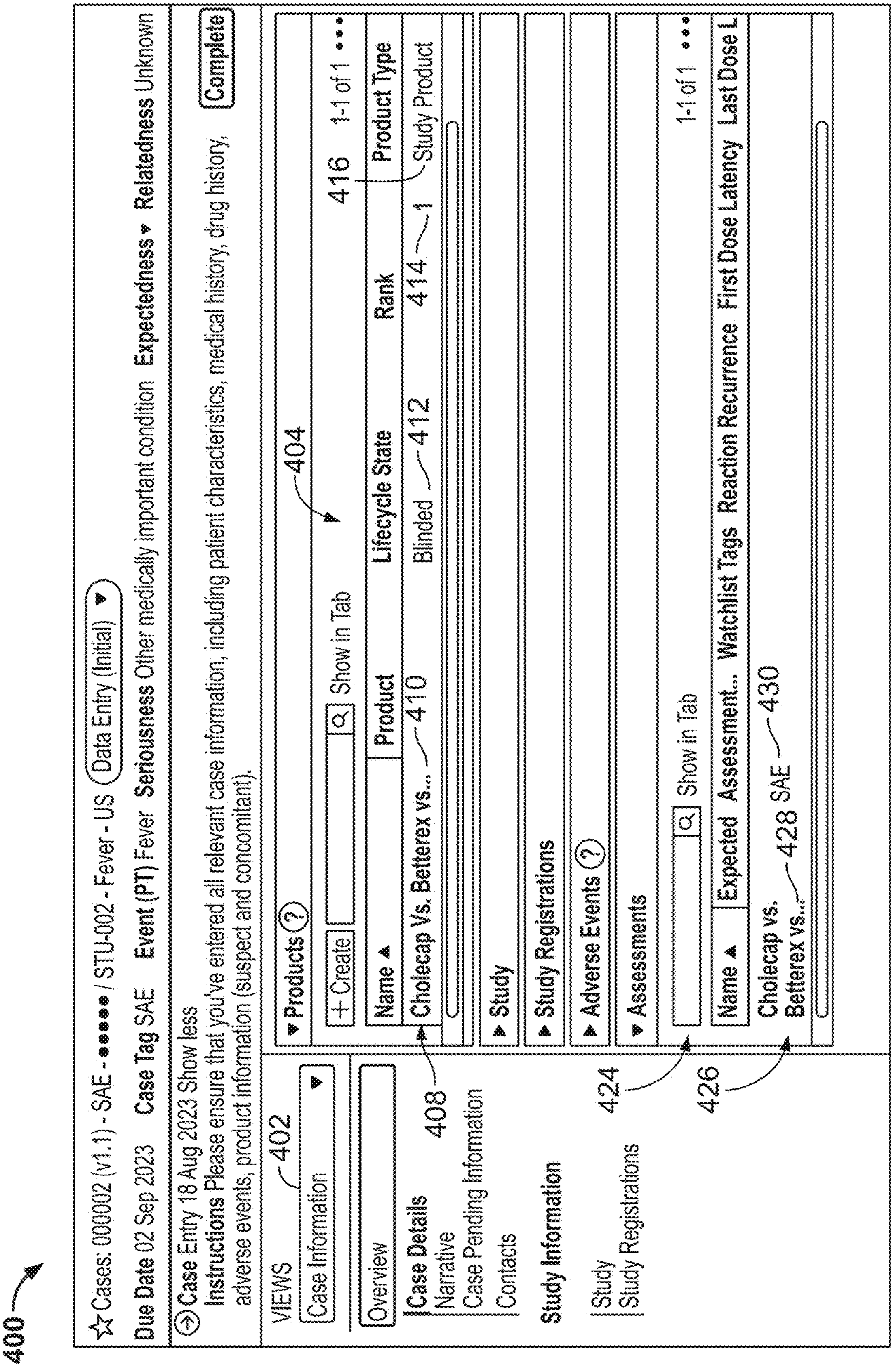
FIGS. 4A-4C may be illustrations of some aspects of a user interface generated by the case dataset intake and management system of FIG. 1 to manage, unblind, and output a case dataset, according to an example embodiment.
Figure 4B:
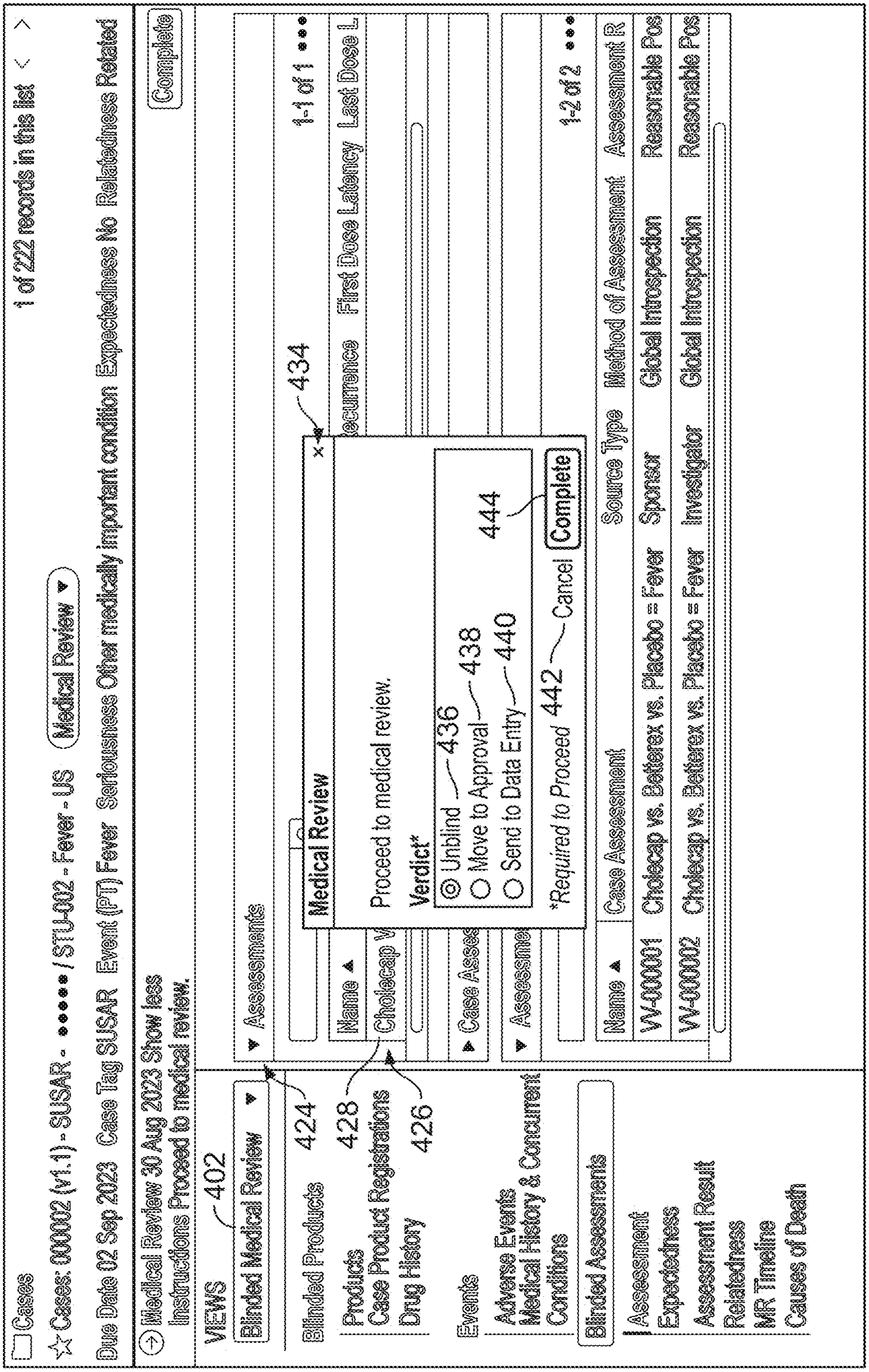
Figure 4C:
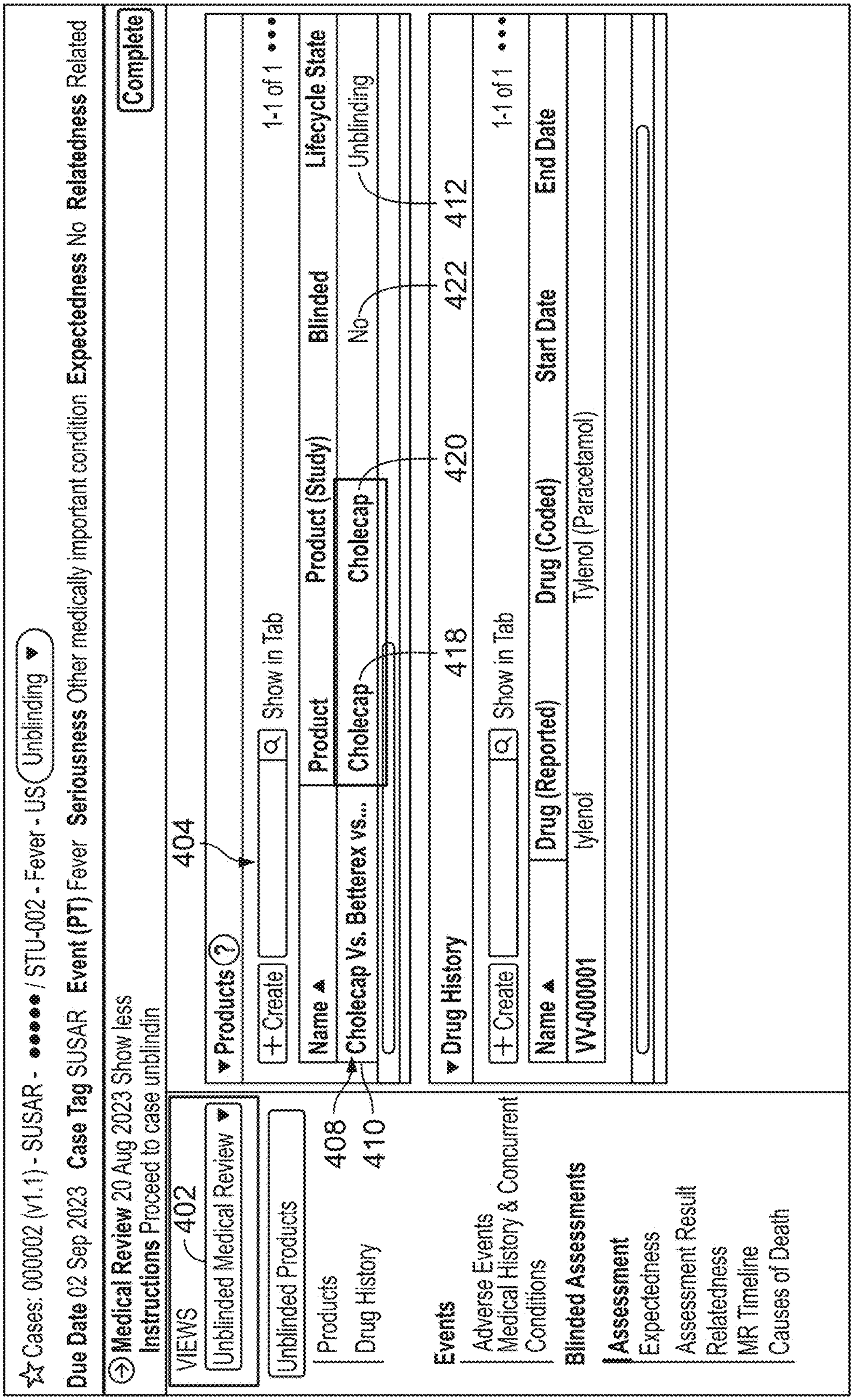

Referring now to FIGS. 4A-4C, the case page 400 which can be displayed on a display of the I/O circuit 162 of the client computing device 108, is shown. In general, the case page 400 provides the user an interface to manage a specific case dataset. As shown, the case page 400 includes a view drop-down box 402, a medical product section 404, an assessment section 424, and an unblind pop-up page 434. To render or generate the case page 400 on the client computing device 108, the provider computing system 104 may provide the case dataset to the client computing device 108. In this regard, it should be understood that each of the fields or buttons of the case page 400 may be or include case data, as described herein.

For example, the view drop-down box 402 may be a selectable drop-down box that, when selected, displays multiple view options (not shown). For a case dataset that includes unblinded medical product data and blinded medical product data, the view drop-down box 402 may include an unblinded view option (see FIG. 4C) and a blinded view option (see FIG. 4B). In response to a selection of the blinded view option, the case page 400 may include and/or display blinded medical product data (see FIGS. 4A-4B). In response to a selection of the unblinded view option, the case page 400 may include and/or display unblinded medical product data (see FIG. 4C).

In some embodiments, the view drop-down box 402 may only include an unblinded view option and/or the case page 400 may only include and/or display unblinded medical product data, in response to the provider computing system 104 determining the client computing device 108 displaying the case page 400 is associated with an account having blind access privileges. For example, to render or generate the case page 400 on the client computing device 108, the provider computing system 104 may determine the client computing device 108 is associated or has provided authentication data associated with an account having blind access privileges. Then, in response, the provider computing system 104 may output or provide the case dataset including the blinded medical product data and the unblinded medical product data to the client computing device 108 for display on the case page 400. Then, in response to a selection of the specific view option (e.g., unblinded, blinded, etc.), the case page 400 may display the respective medical product data. In comparison, if the provider computing system 104 determines the client computing device 108 is associated or has provided authentication data associated with an account not having blind access privileges, the provider computing system 104 may output or provide the case dataset including the blinded medical product data but not the unblinded medical product data to the client computing device 108 for display on the case page 400. Accordingly, the view drop-down box 402 may only include a blinded view option, and the case page 400 may only include and/or display blinded medical product data.

The medical product section 404 may provide the user of the respective client computing device 108 with an interface to set, manage, and update the medical products of the case dataset of the case page 400. For instance, the medical product section 404 includes one or more medical product representations 408 associated with a specific medical product. Each medical product representation 408 may represent a specific medical product and include a name field 410, a state field 412, a product type field 416, a product field 418, a product study field 420, and a blinded field 422. When the case page 400 includes and/or displays the blinded medical product data, each of the fields 410-422 may include blinded medical product data (e.g., as shown on FIG. 4A). In comparison, when the case page 400 includes and/or displays the blinded medical product data, each of the fields 410-422 may include unblinded medical product data (e.g., as shown on FIG. 4C).

The name field 410 may be a selectable and/or editable field that includes the name of the medical product of the medical product representation 408 which may then be sent by the respective client computing device 108 to the provider computing system 104 for storage. For blinded medical products or medical products associated with a specific study, the name field 410 may include the name of the study (e.g., "Cholecap vs. Placebo," "Cholecap vs. Comparator Drug vs. Placebo, etc.).

The state field 412 may be a field that includes the state (e.g., blinded, unblinded, etc.) of the medical product of the medical product representation 408. Likewise, the blinded field 422 may be a field that indicates whether the medical product data of the medical product representation 408 is blinded or unblinded. For instance, when the unblinded medical product data is displayed on the case page 400, the medical product field 422 may include the term "unblinded." In comparison, when the blinded medical product data is displayed on the case page 400, the medical product field 422 may include the term "blinded."

The product type field 416 may be a field that includes the product type (e.g., over-the-counter (OTC) drug, drug, Vaccine, biologic, placebo, comparator drug, etc.) of the medical product of the medical product representation 408. When the unblinded medical product data is displayed on the case page 400, the product type field 416 may include the specific medical product type of the medical product. In comparison, when the blinded medical product data is displayed on the case page 400, the product type field 416 may include no value or blinded product data (e.g., "***," "1232132121," "token1," etc.).

Similarly, the product field 418 may be a field that includes the product (e.g., "Cholecap," "Drug X" "Vaccine Y," "Sugar Pill Placebo," "Comparator Drug Y," etc.) of the medical product of the medical product representation 408. When the unblinded medical product data is displayed on the case page 400, the product type 418 may include the specific medical product. In comparison, when the blinded medical product data is displayed on the case page 400, the product field 418 may include no value or blinded product data (e.g., "***" "1232132121," "token1," etc.).

The product study field 420 may be a field that includes the study associated with the medical product of the medical product representation 408 (e.g., "Study 123," "Cholecap vs. Placebo," etc.). The product study field 420 may not include or display unblinded medical product data. Accordingly, the product study field 420 may not change when the unblinded medical product data is displayed on the case page 400 versus when the blinded medical product data is displayed on the case page 400.

Still referring to FIGS. 4A-4C, the assessment section 424 may provide the user of the respective client computing device 108 with an interface to set, manage, and update an assessment of the adverse event of the adverse event section (not shown). For instance, the assessment section 424 includes one or more assessment representations 426 associated with a specific assessment of a specific adverse event. Each assessment representations 426 may represent a specific assessment and adverse event and include a name field 428 and an assessment field 430.

The name field 428 may be a selectable and/or editable field that includes the name of the assessment of the assessment representations 426 which may then be sent by the respective client computing device 108 to the provider computing system 104 for storage. Likewise, the assessment field 430 may be a selectable and/or editable field through which the client computing device 108 can set the assessment (e.g., serious adverse event (SAE), serious unexpected suspected adverse event (SUSAR), non-serious expected adverse event, etc.) of the adverse event.

In operation, when performing an assessment (e.g., via the assessment section 424), the user of the client computing device 108 may determine the medical product requires unblinding to determine reportability to health agencies. For instance, the user of the client computing device 108 may perform the assessment and determine the adverse event is a SUSAR, which requires unblinding and determination of reporting to the health agencies (e.g., the FDA). Accordingly, the user may select an unblind button (not shown). In response, the case page 400 may generate and display (and overlay) the unblind pop-up page 434. The unblind pop-up page 434 may include multiple selectable options (e.g., an unblind option 436, a move to approval option 438, a send to data entry option 440, etc.), a cancel button 442, and a complete button 444. The user of the client computing device 108 may select one of the options and then select the complete button 444. If the user has selected the unblind option 436, the client computing device 108 may generate the request to unblind the medical product and provide the request to the provider computing system 104.

In some embodiments, if the client computing device 108 is not associated with an account having unblind privileges and/or blind access privileges, the provider computing system 104 may not provide the unblind button (not shown) or display the unblind pop-up page 434. In other embodiments, if the client computing device 108 is not associated with an account having unblind privileges and/or blind access privileges, the provider computing system 104 may provide provide the unblind button (not shown) and display the unblind pop-up page 434, but not unblind the medical product, in response to receiving the request to unblind the medical product from the client computing device 108.

Figure 5A:
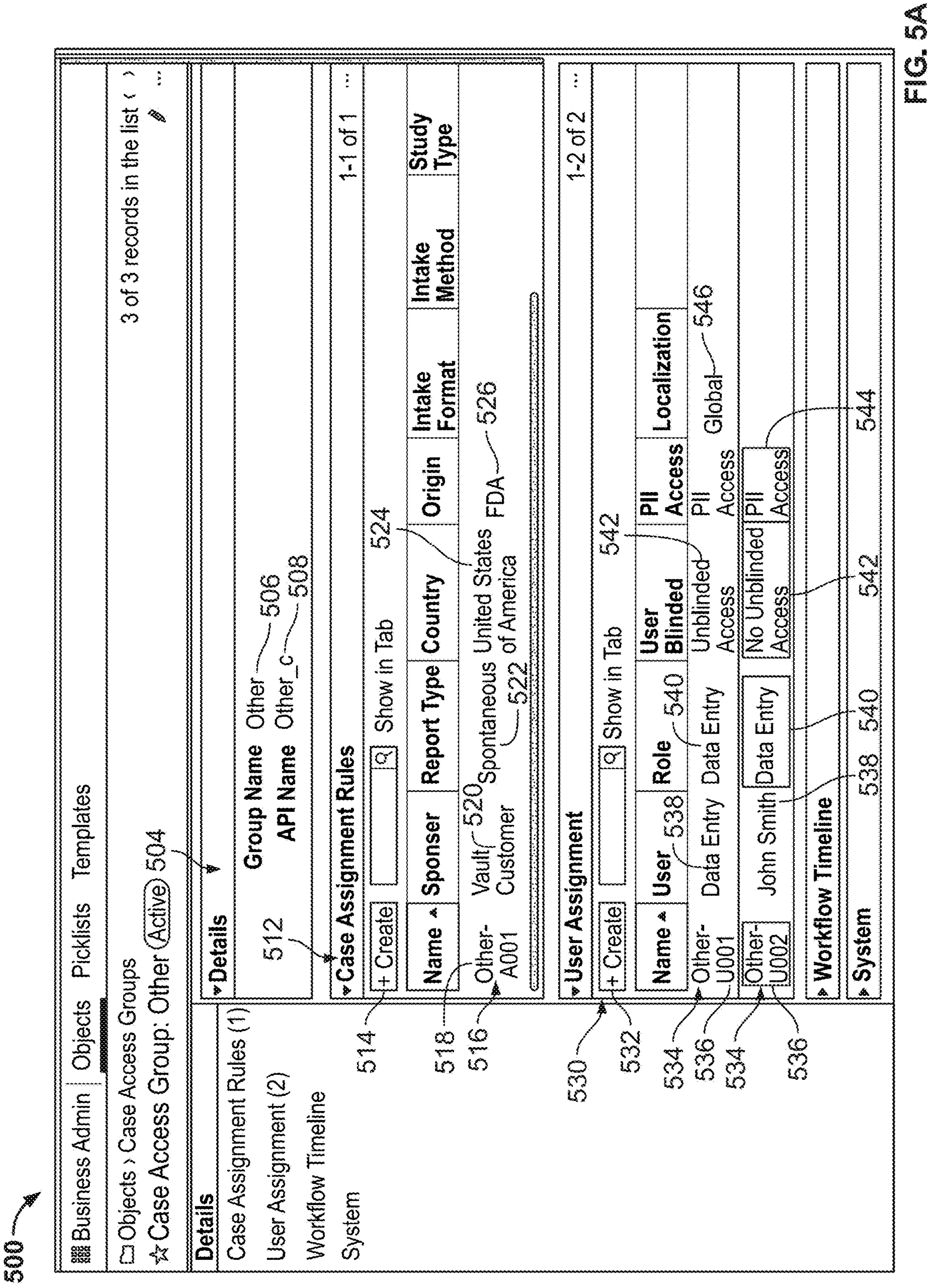
FIGS. 5A-5C may be illustrations of some aspects of a user interface generated by the case dataset intake and management system of FIG. 1 to receive case access group data, according to an example embodiment.
Figure 5B:
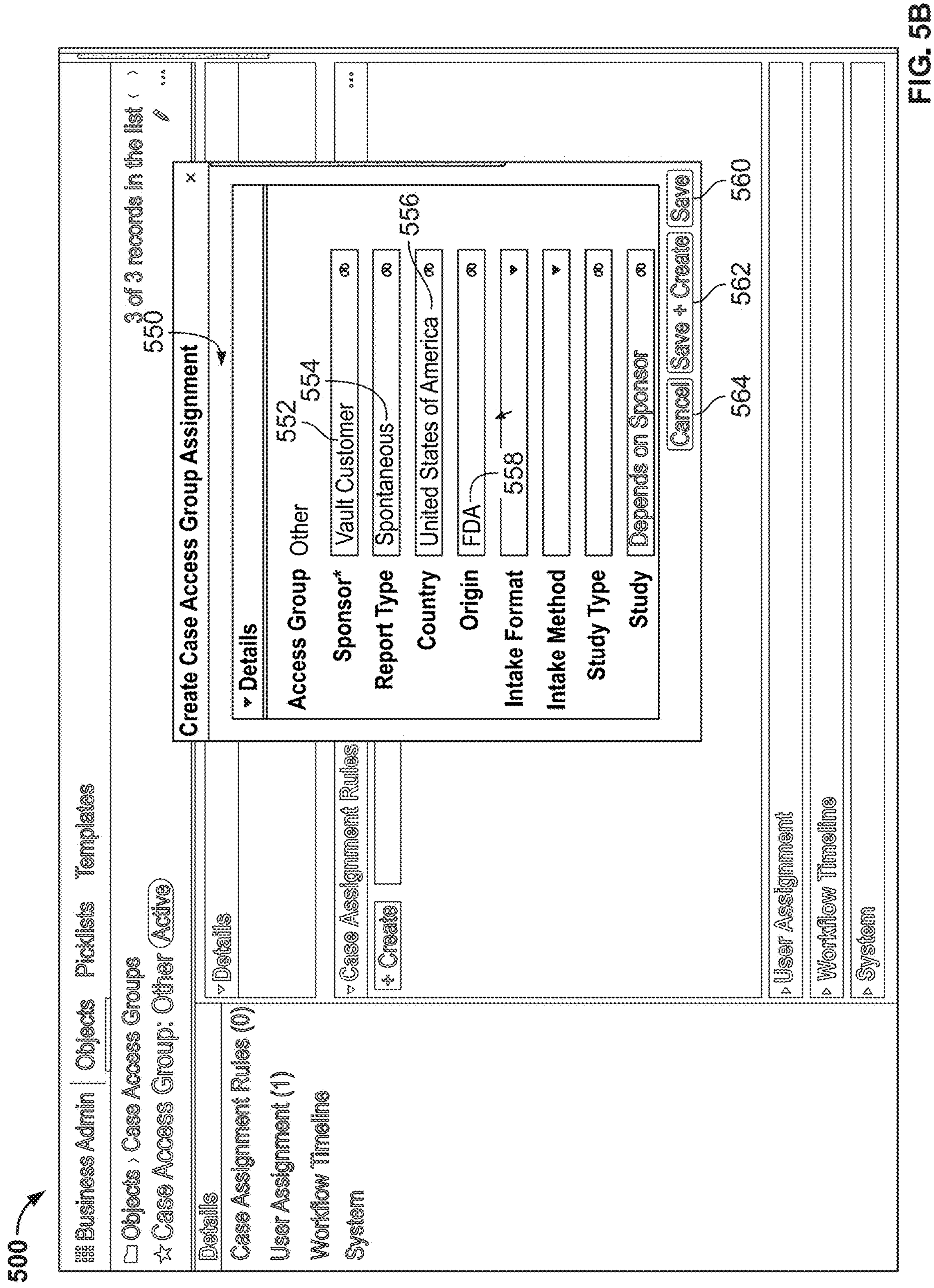
Figure 5C:
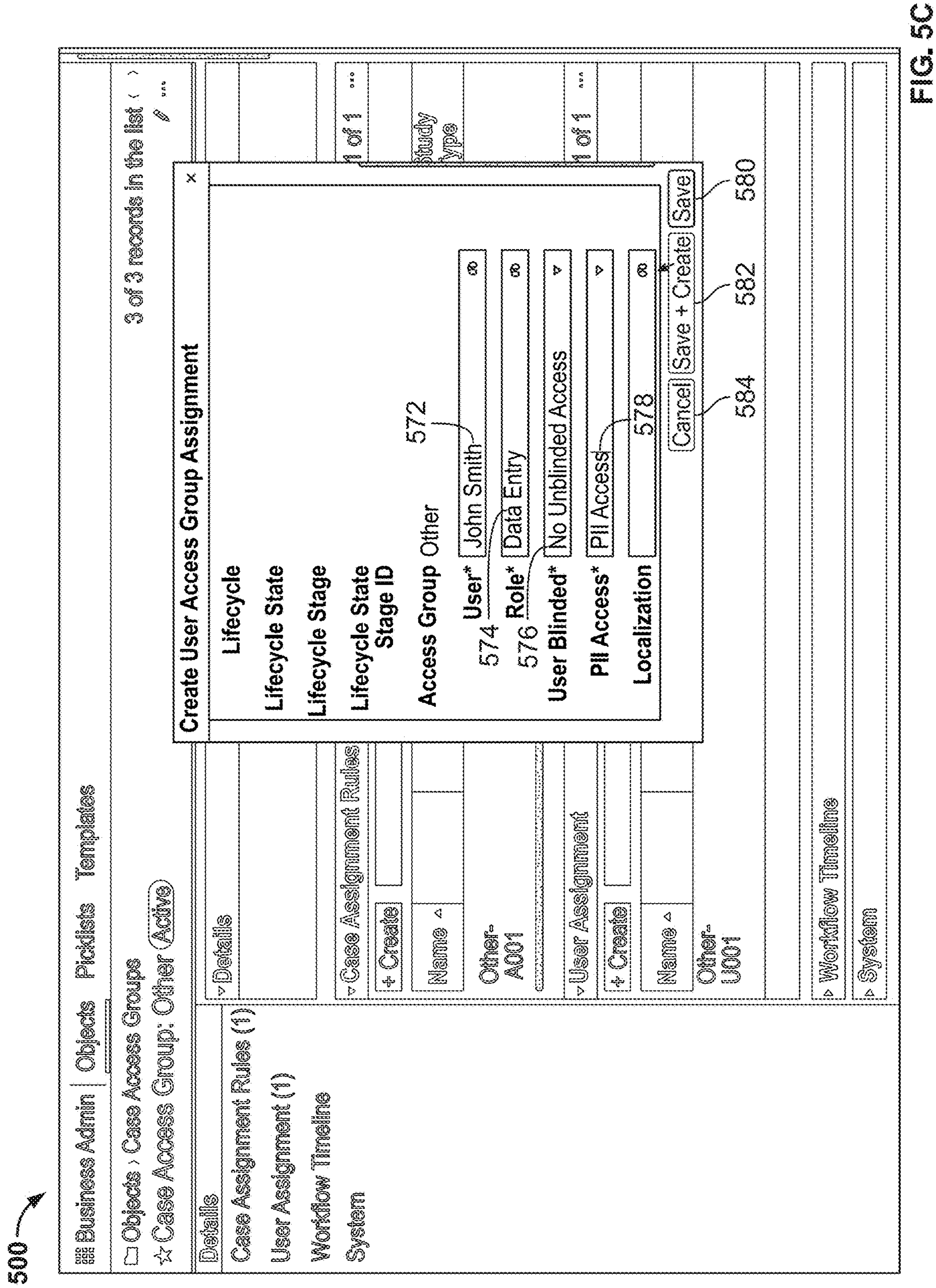

Referring now to FIGS. 5A-5C, a case access group page 500 which can be displayed on a display of the I/O circuit 162 of the client computing device 108 is shown. In general, the case access group page 500 provides the user an interface to setup and manage a specific case access group. As shown, the case access group page 500 includes a details or overview section 504, a case assignment section 512, and a user assignment section 530. To render or generate the case access group page 500 on the client computing device 108, the provider computing system 104 may provide the case access group (including the case assignment data for the case assignment section 512 and the user assignment data for the user assignment section 530) for the specific case access group of the case access group page 500 to the client computing device 108 for display thereon. In this regard, it should be understood that the access group data described herein may include or incorporate the data of the fields 506-578.

The details or overview section 504 provides the user of the respective client computing device 108 with details or an overview of the case access group. As shown, the details or overview section 504 includes a name field 506 and an API field 508. The name field 508 may be a selectable and/or editable field through which the user of the respective client computing device 108 can edit and/or initially set the name of the case access group of the case access group page 500 which may then be sent by the respective client computing device 108 to the provider computing system 104 for storage. Likewise, the API field 508 may be a selectable and/or editable text field through which the user of the respective client computing device 108 can edit and/or initially set a title of the application programming interface (API) data object of the case access group of the case access group page 500 which may then be sent by the respective client computing device 108 to the provider computing system 104 for storage.

The case assignment section 512 provides the user of the respective client computing device 108 with an interface to manage and set the case assignment data or rules associated with the case access group of the case access group page 500. As shown, the case assignment section 512 includes a create or new button 514 and one or more case assignment rule representations 516. The create button 514 is a selectable or clickable button that, when selected, may cause the client computing device 108 to generate a new case assignment ruleset (or generate a request to generate a new case assignment ruleset and provide the request the request to the provider computing system 104). Further, each time the create button 514 is selected, the provider computing system 104 may popup or overlay a case assignment rule generation page or section 550, which will be described further herein.

Each case assignment rule representation 516 represents a specific rule or ruleset which is used to assign case datasets to the case access group (as discussed with regard to the method 300). In this regard, each case assignment rule representation 516 may include a name field 518, a sponsor or customer field 520, a report type field 522, a country field 524, an origin field 526, an intake format field (not shown), an intake method field (not shown), a study type field (not shown), and/or a study field (not shown).

The name field 518 may be a selectable and/or editable field through which the user of the respective client computing device 108 can edit the name of the case assignment rule of the case assignment rule representation 516 which may then be sent by the respective client computing device 108 to the provider computing system 104 for storage. Likewise, the sponsor field 520 may be a selectable and/or editable field through which the user of the respective client computing device 108 can edit the customer or sponsor for which the rule of the case assignment rule representation 516 is associated, which may then be sent by the respective client computing device 108 to the provider computing system 104 for storage. The sponsor field 520 may decide which cases (e.g., which case repository 134) the rule is to be applied to.

The report type field 522 may be a selectable and/or editable field through which the user of the respective client computing device 108 can edit the report type (e.g., spontaneous, study, agency, product testing, etc.) of the case datasets to be included in the case access group of the case access group page 500, which may then be sent by the respective client computing device 108 to the provider computing system 104 for storage.

The country field 524 may be a selectable and/or editable field through which the user of the respective client computing device 108 can edit set the country or region in which the case datasets were reported or took place (e.g., USA, China, Japan, Asia, etc.) to be included in the case access group of the case access group page 500, which may then be sent by the respective client computing device 108 to the provider computing system 104 for storage. Similarly, the origin field 526 may be a selectable and/or editable field through which the user of the respective client computing device 108 can edit the origin (i.e., where the cases were received from (e.g., the client computing device 108, the FDA, the EMA, Worldwide, etc.) of the case datasets to be included in the case access group of the case access group page 500, which may then be sent by the respective client computing device 108 to the provider computing system 104 for storage.

The user assignment section 530 provides the user of the respective client computing device 108 with an interface to manage and set the user assignment data or rules associated with the case access group of the case access group page 500. As shown, the user assignment section 530 includes a create or new button 532 and one or more user assignment rule representations 534. The create button 532 is a selectable or clickable button that, when selected, may cause the client computing device 108 to generate a new user assignment ruleset (or generate a request to generate a new user assignment ruleset and provide the request the request to the provider computing system 104). Further, each time the create button 532 is selected, the provider computing system 104 may popup or overlay the user assignment generation page or section 570, which will be described further herein.

Each user assignment rule representation 534 represents a specific rule or ruleset which is used to assign users (or accounts) to the case access group (as discussed with regard to the method 200). In this regard, each user assignment rule representation 534 may include a name field 536, a user or user(s) field 538, a role field 540, a blind access privilege field 542, a PII access privilege field 544, and a localization field 546.

The name field 536 may be a selectable and/or editable field through which the user of the respective client computing device 108 can edit the name of the user assignment rule of the user assignment rule representation 534 which may then be sent by the respective client computing device 108 to the provider computing system 104 for storage. Likewise, the user field 538 may be a selectable and/or editable field through which the user of the respective client computing device 108 can edit the user or user(s) of the user assignment rule representation 534 which may then be sent by the respective client computing device 108 to the provider computing system 104 for storage. For instance, via the user field 538, the admin may select a specific user or account (e.g., John Smith) or a generic set of users or accounts (e.g., "Data Entry") which may then be defined further via the role field 540.

In this regard, the role field 540 may be a selectable and/or editable field through which the user of the respective client computing device 108 can edit the roles or roles of the users of the of the user assignment rule representation 534 is associated which may then be sent by the respective client computing device 108 to the provider computing system 104 for storage. The role may indicate a job title or position and identify a group of users or accounts that share specific characteristics. For instance, the role "Data Entry" may be associated with accounts that are used for the entry of data into the provider computing system 104.

The blind access privilege field 542 may be a selectable and/or editable field through which the user of the respective client computing device 108 can edit the blind access privileges of the user assignment rule which may then be sent by the respective client computing device 108 to the provider computing system 104 for storage. For instance, via the blind access privilege field 542, the admin may set the blind access privilege of a specific user to "Unblinded Access" or "No Unblinded Access."

Likewise, the PII access privilege field 544 may be a selectable and/or editable field through which the user of the respective client computing device 108 can edit the PII access privileges of the user assignment rule which may then be sent by the respective client computing device 108 to the provider computing system 104 for storage. For instance, via the PII access privilege field 544, the admin may set the PII access privilege of a group of users (e.g., data entry employees) to "PII Access" or "No PII Access."

The localization field 546 may be a selectable and/or editable field through which the user of the respective client computing device 108 can edit the localization of the user assignment rule representation 534 which may then be sent by the respective client computing device 108 to the provider computing system 104 for storage. For instance, via the localization field 546, the user may select a specific localization or region of the users that are to be included in the case access group (e.g., Europe, Asia, USA, Japan). In one example, the user assignment rule representation 534 may include the user field 538 with "Data Entry", the Role field 540 with "Data Entry", and the localization field 546 with "Europe". Accordingly, during the method 300, based on the user assignment data of the case access group data, the provider computing system 104 may select all users or accounts with the title "Data Entry" that are located in the region "Europe".

Referring now to FIG. 5B, the case access group page 500 is shown to include the case assignment rule generation page or section 550. When the user would like to generate a new case assignment rule representation 516, the user may select the create button 514. In response, the client computing device 108 may popup and display the case assignment rule generation section 550 (e.g., displayed in front of the rest of the case access group page 500, as shown). The case assignment rule generation section 550 provides an interface to initially set each of the fields of the new case assignment rule representation 516. As shown the case assignment rule generation section 550 includes a sponsor dropdown box 552, a report type drop down box 554, a country drop down box 556, a origin drop down box 558, an intake format drop down box (not shown), an intake method drop down box (not shown), a study type drop down box (not shown), a study drop down box (not shown), a save button 560, a save and create new button 562, and a cancel button 564.

Referring now to FIG. 5C, the case access group page 500 is shown to include the case user rule generation page or section 570. When the user would like to generate a new user assignment rule representation 534, the user may select the create button 532. In response, the client computing device 108 may popup and display the user rule generation section 570 (e.g., displayed in front of the rest of the case access group page 500, as shown). The user rule generation page or section 570 provides an interface to initially set each of the fields of the new user assignment rule representation 534. As shown the user rule generation page or section 570 includes a user drop down box 572, a role drop down box 574, a blind access privilege drop down box 576, a PII access privilege drop down box 578, a localization drop down box (not shown), a save button 580, a save and create new button 582, and a cancel button 584.

The embodiments described herein have been described with reference to the drawings. The drawings illustrate certain details of specific embodiments that implement the systems, methods, and programs described herein. However, describing the embodiments with drawings should not be construed as imposing on the disclosure any limitations that may be present in the drawings.

It should be understood that no claim element herein is to be construed under the provision of 35 U.S.C § 112 (f), unless the element is expressly recited using the phrase "means for."

As used herein, the term "circuit" may include hardware structured to execute the functions described herein. In some embodiments, each respective "circuit" may include machine-readable media for configuring the hardware to execute the functions described herein. The circuit may be embodied as one or more circuitry components including, but not limited to, processing circuitry, network interfaces, peripheral devices, input devices, output devices, sensors, etc. In some embodiments, a circuit may take the form of one or more analog circuits, electronic circuits (e.g., integrated circuits (IC), discrete circuits, system on a chip (SOC) circuits), telecommunication circuits, hybrid circuits, and any other type of "circuit." In this regard, the "circuit" may include any type of component for accomplishing or facilitating achievement of the operations described herein. For example, a circuit as described herein may include one or more transistors, logic gates (e.g., NAND, AND, NOR, OR, XOR, NOT, XNOR), resistors, multiplexors, registers, capacitors, inductors, diodes, wiring, and so on.

The "circuit" may also include one or more processors communicably coupled to one or more memory or memory devices. In this regard, the one or more processors may execute instructions stored in the memory or may execute instructions otherwise accessible to the one or more processors. In some embodiments, the one or more processors may be embodied in various ways. The one or more processors may be constructed in a manner sufficient to perform at least the operations described herein. In some embodiments, the one or more processors may be shared by multiple circuits (e.g., circuit A and circuit B may comprise or otherwise share the same processor which, in some example embodiments, may execute instructions stored, or otherwise accessed, via different areas of memory). Alternatively or additionally, the one or more processors may be structured to perform or otherwise execute certain operations independent of one or more co-processors. In other embodiments, two or more processors may be coupled via a bus to enable independent, parallel, pipelined, or multi-threaded instruction execution. Each processor may be implemented as one or more general purpose processors, application specific integrated circuits (ASICs), field programmable gate arrays (FPGAs), digital signal processors (DSPs), or other suitable electronic data processing components structured to execute instructions provided by the memory. The one or more processors may take the form of a single core processor, a multi-core processor (e.g., dual core, quad core, etc.), microprocessor, etc. In some embodiments, the one or more processors may be external to the apparatus. For example, the one or more processors may be a remote processor (e.g., a cloud-based processor). Alternatively or additionally, the one or more processors may be internal and/or local to the apparatus. In this regard, a circuit or components thereof may be disposed locally (e.g., as part of a local server, a local computing system) or remotely (e.g., as part of a remote server such as a cloud-based server). To that end, a "circuit" as described herein may include components that are distributed across one or more locations. Further, each of the circuits described herein may be distributed across one or more locations (e.g., each as part of one or more remote servers).

An example system for implementing the overall system or portions of the embodiments might include a general-purpose computing device in the form of computers, including a processing unit, a system memory, and a system bus that couples various system components including the system memory to the processing unit. Each memory device may include non-transient volatile storage media, non-volatile storage media, non-transitory storage media (e.g., one or more volatile and/or non-volatile memories), etc. In some embodiments, the non-volatile storage media may take the form of ROM, flash memory (e.g., flash memory such as NAND, 3D NAND, NOR, 3D NOR), EEPROM, MRAM, magnetic storage, hard disks, optical disks, etc. Combinations of the above are also included within the scope of machine-readable media. In this regard, machine-executable instructions comprise, for example, instructions and data which cause a general purpose computer, special purpose computer, or special purpose processing machine to perform a certain function or group of functions. Each respective memory device may be operable to maintain or otherwise store data relating to the operations performed by one or more associated circuits, including processor instructions and related data (e.g., database components, object code components, script components), in accordance with the example embodiments described herein.

It should also be noted that the term "input devices," as described herein, may include any type of input device including, but not limited to, a keyboard, a keypad, a mouse, a joystick, or other input devices performing a similar function. Comparatively, the term "output device," as described herein, may include any type of output device including, but not limited to, a computer monitor, printer, facsimile machine, or other output devices performing a similar function.

It should be noted that the term "field," as described herein may include any form of an input field through which the user interfaces shown and described may receive input from a user of a computing device. For instance, the term "field" may include a text field, a drop-down box and selectable options, a list box, a lookup box, a search bar, an icon, one or more checkboxes, one or more radio buttons, a button, a toggle, a date field, a slider, and the like. Further, each "field" may include and/or receive data that may be associated with a data object as described herein.

It should be noted that although the diagrams herein may show a specific order and composition of method steps, it is understood that the order of these steps may differ from what is depicted. For example, two or more steps may be performed concurrently or with partial concurrence. Also, some method steps that are performed as discrete steps may be combined, steps being performed as a combined step may be separated into discrete steps, the sequence of certain processes may be reversed or otherwise varied. The order or sequence of any element or apparatus may be varied or substituted according to alternative embodiments. Accordingly, all such modifications are intended to be included within the scope of the present disclosure as defined in the appended claims. Such variations will depend on the machine-readable media and hardware systems chosen and on designer choice. It is understood that all such variations are within the scope of the disclosure. Likewise, software and web implementations of the present disclosure could be accomplished with standard programming techniques with rule-based logic and other logic to accomplish the various database searching steps, correlation steps, comparison steps, and decision steps.

The foregoing description of embodiments has been presented for purposes of illustration and description. It is not intended to be exhaustive or to limit the disclosure to the precise form disclosed, and modifications and variations are possible in light of the above teachings or may be acquired from this disclosure. The embodiments were chosen and described in order to explain the principles of the disclosure and its practical application to enable one skilled in the art to utilize the various embodiments and with various modifications as are suited to the particular use contemplated. Other substitutions, modifications, changes, and omissions may be made in the design, operating conditions and embodiment of the embodiments without departing from the scope of the present disclosure as expressed in the appended claim.

What is claimed is:

1. A method for generating a case dataset in a case dataset intake and management system, wherein the case intake and management system comprises a provider computing comprising a first repository for storing case datasets, the method comprising:

receiving, by the provider computing system, a source file including blinded medical product data;

determining, by the provider computing system, case data including the blinded medical product data based on the source file;

generating, by the provider computing system, the case dataset including the case data;

generating, by the provider computing system, a copy of the blinded medical product data;

modifying, by the provider computing system, the copy of the blinded medical product data to generate unblinded medical product data;

adding, by the provider computing system, the unblinded medical product data to the case data of the case dataset;

storing, by the provider computing system, the case dataset in the first repository; and outputting, by the provider computing system, the case dataset including a portion of the case data, wherein the portion of the case data includes the blinded medical product data and does not include the unblinded medical product data.

2. The method of claim 1, further comprising:

receiving, by the provider computing system, client computing device authentication data;

authenticating, by the provider computing system, the client computing device authentication data; and determining, by the provider computing system, the client computing device authentication data is associated with an account not including a blind access privilege, wherein, in response to the authentication data being associated with the account not including a blind access privilege, the case dataset is output including the portion of the case data.

3. The method of claim 2, wherein the provider computing system includes a second repository for storing account data including trusted authentication data, and wherein determining the client computing device authentication data is associated with an account not including a blind access privilege comprises:

searching, by the provider computing system, the second repository for account data including trusted authentication data matching the received client computing device authentication data; and determining, by the provider computing system and in response to returning matching account data, the account data does not include a blind access privilege.

4. The method of claim 2, wherein the client computing device authentication data is received from an electronic address, and wherein authenticating the client computing device authentication data comprises:

generating, by the provider computing system, a limited-use key (LUK); and assigning, by the provider computing system, the LUK to the electronic address, and wherein the method further comprises:

receiving, by the provider computing system, a request to output the case dataset including the LUK.

5. The method of claim 2, wherein the client computing device authentication data is received from a client computing device, and wherein the case dataset is output to the client computing device to enable display on a user interface, wherein the user interface includes:

a view drop-down box including a blinded view option; and a medical product section including at least a portion of the blinded medical product data.

6. The method of claim 1, wherein the source file further includes reporter data and an adverse event code, and wherein the determined case data further includes the reporter data and the adverse event data.

7. The method of claim 1, wherein modifying the copy of the blinded medical product data to generate the unblinded medical product data comprises:

outputting, by the provider computing system, a request for unblinded medical product data;

receiving, by the provider computing system and in response to outputting the request, the unblinded medical product data; and generating, by the provider computing system, the unblinded medical product data by modifying the copy of the blinded medical product data to include the unblinded medical product data.

8. The method of claim 1, wherein the blinded medical product data is first blinded medical product data, wherein the source file further includes unblinded medical product data, and wherein the method further comprises:

modifying, by the provider computing system, the unblinded medical product data of the source file to generate second blinded medical product data.

9. The method of claim 8, wherein the provider computing system includes a second repository for storing medical product data, and wherein modifying the unblinded medical product data of the source file to generate the second blinded medical product data comprises:

generating, by the provider computing system, the second blinded medical product data including at least one token based on the unblinded medical product data; and storing, by the provider computing system, the unblinded medical product data in the second repository.

10. The method of claim 8, wherein modifying the unblinded medical product data of the source file to generate the second blinded medical product data comprises:

generating, by the provider computing system, the second blinded medical product data by encrypting the unblinded medical product data.

11. A method for generating a case dataset in a case dataset intake and management system, wherein the case intake and management system comprises a provider computing comprising a first repository for storing case datasets, the method comprising:

receiving, by the provider computing system, a source file including blinded medical product data;

determining, by the provider computing system, case data including reporter data, an adverse event code, and the blinded medical product data based on the source file;

generating, by the provider computing system, the case dataset including the case data;

generating, by the provider computing system, a copy of the blinded medical product data;

modifying, by the provider computing system, the copy of the blinded medical product data to generate unblinded medical product data;

adding, by the provider computing system, the unblinded medical product data to the case data of the case dataset;

storing, by the provider computing system, the case dataset in the first repository; and outputting, by the provider computing system, the case dataset including a portion of the case data, wherein the portion of the case data includes the unblinded medical product data and the blinded medical product data.

12. The method of claim 11, further comprising:

receiving, by the provider computing system, client computing device authentication data;

authenticating, by the provider computing system, the client computing device authentication data; and determining, by the provider computing system, the client computing device authentication data is associated with an account including a blind access privilege, wherein, in response to the authentication data being associated with the account including a blind access privilege, the case dataset is output including the portion of the case data.

13. The method of claim 12, wherein the provider computing system includes a second repository for storing account data including trusted authentication data, and wherein determining the client computing device authentication data is associated with an account including a blind access privilege comprises:

searching, by the provider computing system, the second repository for account data including trusted authentication data matching the received client computing device authentication data; and determining, by the provider computing system and in response to returning matching account data, the account data includes a blind access privilege.

14. The method of claim 12, wherein the client computing device authentication data is received from an electronic address, and wherein authenticating the client computing device authentication data comprises:

generating, by the provider computing system, a limited-use key (LUK); and assigning, by the provider computing system, the LUK to the address, and wherein the method further comprises:

receiving, by the provider computing system, a request to output the case dataset including the LUK.

15. The method of claim 12, wherein the client computing device authentication data is received from a client computing device, and wherein the case dataset is output to the client computing device to enable display on a user interface, wherein the user interface includes:

a view drop-down box including an unblinded view option and a blinded view option; and a medical product section, wherein in response to a selection of the unblinded view option the medical product section includes at least a portion of the unblinded medical product data, and wherein in response to a selection of the blinded view option the medical product section includes at least a portion of the blinded medical product data.

16. The method of claim 11, wherein modifying the copy of the blinded medical product data to generate the unblinded medical product data comprises:

outputting, by the provider computing system, a request for unblinded medical product data;

receiving, by the provider computing system and in response to outputting the request, the unblinded medical product data; and generating, by the provider computing system, the unblinded medical product data by modifying the copy of the blinded medical product data to include the unblinded medical product data.

17. The method of claim 11, wherein the request to unblind the medical product data includes authentication data, and wherein modifying the copy of the blinded medical product data to generate the unblinded medical product data comprises:

outputting, by the provider computing system, a request for unblinded medical product data including the authentication data;

receiving, by the provider computing system and in response to outputting the request, the unblinded medical product data; and generating, by the provider computing system, the unblinded medical product data by modifying the copy of the blinded medical product data to include the unblinded medical product data.

18. The method of claim 11, wherein the provider computing system includes a second repository for storing account data including associated with a plurality of accounts, and wherein the method further comprises:

receiving, by the provider computing system, access group data associated with an access group and including case assignment data, user assignment data, and blind access privilege data;

assigning, by the provider computing system, a plurality of case datasets of the first repository including the case dataset to the access group based on the case assignment data;

assigning, by the provider computing system, one or more accounts of the second repository to the access group based on the user assignment data;

determining, by the provider computing system, the client computing device authentication data is associated with an account including a blind access privilege based on the account being assigned to the access group, wherein, in response to the authentication data being associated with the account including a blind access privilege, the case dataset is output including the portion of the case data.

* * * * *